(12) United States Patent
Benz et al.

(10) Patent No.: US 11,931,312 B2
(45) Date of Patent: Mar. 19, 2024

(54) USER INTERFACE FOR A PATIENT SUPPORT APPARATUS WITH INTEGRATED PATIENT THERAPY DEVICE

(71) Applicant: Hill-Rom Services, Inc., Batesville, IN (US)

(72) Inventors: Eric D. Benz, Batesville, IN (US); John G. Byers, Batesville, IN (US); Scott M. Corbin, Sunman, IN (US); Richard H. Heimbrock, Cary, NC (US); Michael A. Knecht, Batesville, IN (US); Bradley T. Smith, Raleigh, NC (US); Lori Ann Zapfe, Milroy, IN (US); Robert M. Zerhusen, Batesville, IN (US); Kenneth L. Lilly, West Chester, OH (US); Jonathan D. Turner, Batesville, IN (US); James L. Walke, Batesville, IN (US); Joseph T. Canter, Harrison, OH (US); Richard J. Schuman, Sr., Cary, NC (US); John V. Harmeyer, Cleves, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 915 days.

(21) Appl. No.: 16/829,637

(22) Filed: Mar. 25, 2020

(65) Prior Publication Data
US 2020/0306127 A1    Oct. 1, 2020

Related U.S. Application Data

(60) Provisional application No. 62/826,785, filed on Mar. 29, 2019.

(51) Int. Cl.
*A61H 9/00* (2006.01)
*A61G 7/05* (2006.01)
*G16H 10/60* (2018.01)

(52) U.S. Cl.
CPC ............ *A61H 9/0071* (2013.01); *A61G 7/05* (2013.01); *A61H 9/0078* (2013.01);
(Continued)

(58) Field of Classification Search
CPC .... A61H 9/005; A61H 9/0071; A61H 9/0078; A61H 9/0092; A61H 2201/0103;
(Continued)

(56) References Cited

U.S. PATENT DOCUMENTS

| 4,396,010 A | 8/1983 | Arkans |
| 4,479,494 A | 10/1984 | McEwen |

(Continued)

FOREIGN PATENT DOCUMENTS

| EP | 2374440 A2 | 10/2011 |
| EP | 3207911 A1 | 8/2017 |

(Continued)

*Primary Examiner* — Colin W Stuart
*Assistant Examiner* — Matthew R Moon
(74) *Attorney, Agent, or Firm* — Barnes & Thornburg LLP

(57) ABSTRACT

A therapy system includes a patient support apparatus and a pneumatic therapy device that is coupleable to the patient support apparatus. The therapy device may receive power and air flow from the patient support apparatus.

23 Claims, 18 Drawing Sheets

(52) U.S. Cl.
CPC ..... *G16H 10/60* (2018.01); *A61H 2201/0103* (2013.01); *A61H 2201/0142* (2013.01); *A61H 2201/1409* (2013.01); *A61H 2201/165* (2013.01); *A61H 2201/5023* (2013.01); *A61H 2205/106* (2013.01); *A61H 2209/00* (2013.01); *A61H 2230/805* (2013.01)

(58) Field of Classification Search
CPC .... A61H 2201/0107; A61H 2201/0142; A61H 2201/0184; A61H 2201/0214; A61H 2201/0242; A61H 2201/025; A61H 2201/1409; A61H 2201/0146; A61H 2201/165; A61H 2201/5007; A61H 2201/501; A61H 2203/0443; A61H 2205/10; A61H 2205/106; A61H 2209/00; A61H 2230/0443; A61H 2230/805; A61G 7/05; G16H 10/60; A47C 21/08; A47D 7/00

See application file for complete search history.

(56) References Cited

U.S. PATENT DOCUMENTS

| | | | |
|---|---|---|---|
| 5,771,511 | A | 6/1998 | Kummer et al. |
| 5,781,949 | A | 7/1998 | Weismiller et al. |
| 6,876,303 | B2 | 4/2005 | Reeder et al. |
| 6,877,572 | B2 | 4/2005 | Ruschke et al. |
| 6,987,448 | B2 | 1/2006 | Dubisar et al. |
| 7,480,951 | B2 | 1/2009 | Ulrich et al. |
| 7,641,623 | B2 | 1/2010 | Biondo et al. |
| 8,679,040 | B2 | 3/2014 | Horst |
| 8,752,220 | B2 | 6/2014 | Soderberg et al. |
| 8,845,562 | B2 | 9/2014 | Receveur et al. |
| 9,017,273 | B2 | 4/2015 | Burbank et al. |
| 9,237,979 | B2 | 1/2016 | Carnell et al. |
| 9,492,341 | B2 | 11/2016 | Huster et al. |
| 9,539,155 | B2 | 1/2017 | Johannigman et al. |
| 9,655,457 | B2 * | 5/2017 | Meyer .................. A47C 27/088 |
| 9,737,454 | B2 * | 8/2017 | Hornbach ............ A61B 5/0295 |
| 9,827,157 | B2 | 11/2017 | Newkirk et al. |
| 9,833,369 | B2 | 12/2017 | Chiacchira et al. |
| 10,166,166 | B1 | 1/2019 | Theriot et al. |
| 10,391,019 | B2 | 8/2019 | Stryker et al. |
| 10,403,401 | B2 | 9/2019 | Brosnan et al. |
| 10,410,500 | B2 | 9/2019 | Derenne et al. |
| 10,507,158 | B2 | 12/2019 | Brzenchek et al. |
| 10,517,784 | B2 | 12/2019 | Zerhusen et al. |
| 10,561,549 | B2 | 2/2020 | Walton et al. |
| 10,709,624 | B2 | 7/2020 | Bhimavarapu et al. |
| 11,071,666 | B2 | 7/2021 | Emmons et al. |
| 11,246,776 | B2 | 2/2022 | Moreno et al. |
| 11,273,088 | B2 | 3/2022 | Newkirk et al. |
| 2002/0042583 | A1 | 4/2002 | Barak et al. |
| 2003/0061664 | A1 | 4/2003 | Salvatini et al. |
| 2004/0106884 | A1 | 6/2004 | Bolam et al. |
| 2005/0159690 | A1 | 7/2005 | Barak et al. |
| 2005/0235988 | A1 | 10/2005 | Hansen et al. |
| 2006/0004245 | A1 | 1/2006 | Pickett et al. |
| 2006/0016012 | A1 | 1/2006 | Liu |
| 2008/0172789 | A1 | 7/2008 | Elliot et al. |
| 2008/0249444 | A1 | 10/2008 | Avitable et al. |
| 2009/0177184 | A1 | 7/2009 | Christensen et al. |
| 2010/0042026 | A1 | 2/2010 | Kloecker et al. |
| 2010/0095462 | A1 * | 4/2010 | Bobey ................ A61G 7/05776 5/713 |
| 2011/0030141 | A1 | 2/2011 | Soderberg et al. |
| 2011/0247135 | A1 | 10/2011 | Herman et al. |
| 2012/0277789 | A1 | 11/2012 | Caldarone et al. |
| 2013/0074262 | A1 * | 3/2013 | Receveur ............. A61G 7/0527 177/1 |
| 2013/0338552 | A1 | 12/2013 | Malhi |
| 2013/0340169 | A1 | 12/2013 | Zerhusen et al. |
| 2014/0142473 | A1 | 5/2014 | Lowe et al. |
| 2014/0236058 | A1 | 8/2014 | Lee |
| 2014/0276288 | A1 | 9/2014 | Randolph et al. |
| 2014/0277252 | A1 | 9/2014 | Hyde et al. |
| 2016/0175184 | A1 | 6/2016 | Arkans et al. |
| 2017/0046620 | A1 | 2/2017 | Morrison |
| 2017/0086598 | A1 * | 3/2017 | Ohno ................... G05D 7/0676 |
| 2017/0239131 | A1 * | 8/2017 | Brzenchek .......... A47C 21/048 |
| 2017/0273851 | A1 | 9/2017 | Larmer et al. |
| 2018/0042763 | A1 | 2/2018 | Galer et al. |
| 2018/0272147 | A1 | 9/2018 | Freeman et al. |
| 2018/0350464 | A1 | 12/2018 | Bhimavarapu et al. |
| 2018/0369039 | A1 | 12/2018 | Titov et al. |
| 2019/0000329 | A1 | 1/2019 | Denson et al. |
| 2019/0015289 | A1 | 1/2019 | Grimoldby et al. |
| 2019/0021924 | A1 | 1/2019 | Trepanier et al. |
| 2020/0113773 | A1 | 4/2020 | Ramanan et al. |
| 2020/0121546 | A1 | 4/2020 | Theriot et al. |
| 2020/0253813 | A1 | 8/2020 | Kuhns |

FOREIGN PATENT DOCUMENTS

| | | | |
|---|---|---|---|
| EP | 3231407 A1 * | 10/2017 | ........... A61B 5/1118 |
| EP | 3207911 B1 | 4/2019 | |
| EP | 3714857 A1 | 9/2020 | |
| KR | 20090004859 U | 5/2009 | |
| WO | 2004091463 A2 | 10/2004 | |
| WO | 2014066077 A1 | 5/2014 | |
| WO | 2016003859 A1 | 1/2016 | |
| WO | 2016123595 A1 | 8/2016 | |
| WO | 2019145946 A1 | 8/2019 | |
| WO | 2020206673 A1 | 10/2020 | |

* cited by examiner

USER INTERFACE FOR A PATIENT SUPPORT APPARATUS WITH INTEGRATED PATIENT THERAPY DEVICE

CROSS-REFERENCE TO RELATED APPLICATIONS

This application claims priority under 35 U.S.C. § 119(e) to U.S. Provisional Application No. 62/826,785, filed Mar. 29, 2019, which is expressly incorporated by reference herein.

BACKGROUND

The present disclosure relates to patient support apparatuses such as patient beds and particularly, to patient support apparatuses that have therapy devices. More particularly, the present disclosure relates to patient support apparatuses that have integrated limb compression devices.

Patient support apparatuses, such as patient beds, are used in patient rooms to support sick patients and to support patients recovering from surgery, for example. It is desirable for some patients to wear limb compression sleeves, such as foot sleeves, calf sleeves, thigh sleeves, or a combination of these sleeves. The sleeves are inflated and deflated intermittently to promote blood flow within the patient's limb or limbs thereby helping to prevent deep vein thrombosis, for example. Usually, a separate control box which houses the pneumatic components that operate to inflate and deflate the compression sleeve(s) worn by the patient is provided.

Oftentimes, the control box for the compression sleeve(s) is hung on the footboard of the patient bed. Thus, there is a risk that the control box can slip off of the footboard. Also, relatively long power cords are required to be routed from the control box at the foot end of the bed to a power outlet near the head end of the bed or elsewhere in the patient room. The foot ends of patient beds are typically oriented more toward the center of a room and not adjacent to any room wall. The power cord, therefore, may pose a tripping hazard for caregivers, patients, and visitors. The power cord also may be in the way of other carts or wheeled stands, such as those used to support IV pumps and bags, for example. When not in use, the control box must be stored separately within a healthcare facility.

There is an ongoing need to reduce the labor required for caregivers to deliver quality patient care. Further, there is an ongoing need for the cost of healthcare to be reduced. Finally, the comfort of a person in a clinical environment is directly related to their perception of the quality of their care and their recovery. A therapy system that provides patient comfort, reduced cost, and improved caregiver efficiency addresses the aforementioned needs.

SUMMARY

The present application discloses one or more of the features recited in the appended claims and/or the following features which, alone or in any combination, may comprise patentable subject matter.

According to a first aspect of the present disclosure, a therapy system comprises a pneumatic therapy device and a patient support apparatus. The pneumatic therapy device includes a compression sleeve and a conduit having a first end coupled to the compressions sleeve and a second end. The patient support apparatus includes a frame including a scale, a source of pressurized air, a distribution system and a controller. The distribution assembly includes a conduit for directing a flow of pressurized air from the source of pressurized air, an outlet coupleable to the second end of the conduit of the pneumatic therapy device, and a sensor for detecting a pressure. The controller includes a processor and a memory device, the memory device including instructions that are executable by the processor to control the source of pressurized air, distribution system, and user interface. The instructions cause the controller to be operable to determine the weight of a patient on the frame with the scale system, correlate the weight of the patient with an amount of pressure to be applied to the patient by the pneumatic therapy device, and operate the source of pressurized air and distribution assembly to operate the pneumatic therapy device at correlated pressure.

In some embodiments of the first aspect, the memory device may include further instructions that, when executed by the processor, cause the controller to monitor the pressure in the sleeve of the pneumatic therapy device and the weight of the patient and use the pressure and weight together as inputs into a control algorithm for controlling the operation of the pneumatic therapy device.

In some embodiments of the first aspect, the memory device may include further instructions that, when executed by the processor, cause the controller to determine if the pressure in the sleeve of the pneumatic therapy device meets a pre-programmed correlation with the weight sensed by the scale system, and, if it does, continue to operate the pneumatic therapy device based on the pre-programmed correlation.

In some embodiments of the first aspect, the memory device may include further instructions that, when executed by the processor, cause the controller to determine if the pressure in the sleeve of the pneumatic therapy device meets a pre-programmed correlation with the weight sensed by the scale system, and, if it does not, determine whether the patient has exited the bed.

In some embodiments of the first aspect, the memory device may include further instructions that, when executed by the processor, cause the controller, in response to determining that the patient has not exited the bed, adjust the pressure within the sleeve to match with the pre-programmed correlation to the weight of the patient.

In some embodiments of the first aspect, the memory device may include further instructions that, when executed by the processor, cause the controller, in response to determining that the patient has exited the bed, provide an alert to a caregiver that the pneumatic therapy devise is not being used properly and automatically chart the condition in an electronic medical records system.

In some embodiments of the first aspect, the memory device may further instructions that, when executed by the processor, cause the controller, in response to determining that the patient has exited the bed, to automatically chart the condition in an electronic medical records system.

According to a second aspect of the present disclosure, a method of operating a therapy system that includes a pneumatic therapy device a including a compression, a patient support apparatus, the patient support apparatus including a frame including a scale system, a source of pressurized air, and an air distribution assembly comprises the steps of determining the weight of a patient on the frame with the scale system, correlating the weight of the patient with an amount of pressure to be applied to the patient by the pneumatic therapy device, and operate the source of pressurized air and distribution assembly to operate the pneumatic therapy device at correlated pressure.

In some embodiments of the second aspect, the method includes monitoring the pressure in the sleeve of the pneumatic therapy device and the weight of the patient and use the pressure and weight together as inputs into a control algorithm for controlling the operation of the pneumatic therapy device.

In some embodiments of the second aspect, the method includes determining if the pressure in the sleeve of the pneumatic therapy device meets a pre-programmed correlation with the weight sensed by the scale system, and if it does, continuing to operate the pneumatic therapy device based on the pre-programmed correlation.

In some embodiments of the second aspect, the method includes determining if the pressure in the sleeve of the pneumatic therapy device meets a pre-programmed correlation with the weight sensed by the scale system, and, if it does not, determining whether the patient has exited the bed.

In some embodiments of the second aspect, the method includes, in response to determining that the patient has not exited the bed, adjusting the pressure within the sleeve to match with the pre-programmed correlation to the weight of the patient.

In some embodiments of the second aspect, the method includes, in response to determining that the patient has exited the bed, provide an alert to a caregiver that the pneumatic therapy devise is not being used properly and automatically charting the condition in an electronic medical records system.

In some embodiments of the second aspect, the method includes, in response to determining that the patient has exited the bed, to automatically charting the condition in an electronic medical records system.

In some embodiments of the second aspect, the method includes determining if the pressure in the sleeve of the pneumatic therapy device meets a pre-programmed correlation with the weight sensed by the scale system, and, if it does, continuing to monitor the weight of the patient and the pressure in the sleeve.

According to a third aspect of the present disclosure, a therapy system comprises, a hospital information system, a pneumatic therapy device, and a patient support apparatus. The hospital information system includes an electronic medical records system. The pneumatic therapy device includes a compression sleeve and a conduit having a first end coupled to the compressions sleeve and a second end. The patient support apparatus includes a frame including a scale system, a source of pressurized air, a distribution assembly, and a controller. The distribution assembly includes a conduit for directing a flow of pressurized air from the source of pressurized air, an outlet coupleable to the second end of the conduit of the pneumatic therapy device, and a sensor for detecting a pressure. The controller includes a processor and a memory device. The memory device includes instructions that are executable by the processor to control the source of pressurized air, distribution system, and user interface, and communicate with the hospital information system. The instructions cause the controller to be operable to identify a therapy order in the hospital information system for a pneumatic therapy protocol for a particular patient positioned on the patient support apparatus, receive a command regarding the therapy to be conducted for the patient, and determine whether the pneumatic therapy device is ready to provide the therapy.

In some embodiments of the third aspect, the memory device may include further instructions that, when executed by the processor, cause the controller to, in response to determining that the pneumatic therapy device is ready to provide therapy, automatically start the therapy protocol.

In some embodiments of the third aspect, the memory device may include further includes a user interface in electrical communication with the controller, and wherein the memory device includes instructions that, when executed by the processor, cause the controller to display that status of the therapy protocol on the user interface.

In some embodiments of the third aspect, the therapy system may further include a user interface in electrical communication with the controller, and wherein the memory device includes instructions that, when executed by the processor, cause the controller to communicate the operation of the therapy protocol to the hospital information system for storage in the electronic medical records system.

In some embodiments of the third aspect, the memory device may include further instructions that, when executed by the processor, cause the controller to, in response to determining that the pneumatic therapy device is not ready to provide therapy, generate an alert that the therapy protocol is waiting on a set-up of the pneumatic therapy device.

In some embodiments of the third aspect, the memory device may include further instructions that, when executed by the processor, cause the controller to monitor for an indication that the alert has been responded to by a user and, if the pneumatic device is ready to use, automatically starting the therapy protocol.

According to a fourth aspect of the present disclosure, a method of operating a therapy system that includes a hospital information system having an electronic medical records system, a pneumatic therapy device a including a compression, a patient support apparatus, the patient support apparatus including a frame including a scale system, a source of pressurized air, a display and an air distribution assembly, the method comprising the steps of identifying a therapy order in the hospital information system for a pneumatic therapy protocol for a particular patient positioned on the patient support apparatus, receiving a command regarding the therapy to be conducted for the patient, and determining whether the pneumatic therapy device is ready to provide the therapy.

In some embodiments of the fourth aspect, the method includes, in response to determining that the pneumatic therapy device is ready to provide therapy, automatically starting the therapy protocol.

In some embodiments of the fourth aspect, the method includes displaying that status of the therapy protocol on the user interface.

In some embodiments of the fourth aspect, the method includes communicating the operation of the therapy protocol to the hospital information system for storage in the electronic medical records system.

In some embodiments of the fourth aspect, the method includes, in response to determining that the pneumatic therapy device is not ready to provide therapy, generating an alert that the therapy protocol is waiting on a set-up of the pneumatic therapy device.

In some embodiments of the fourth aspect, the method includes monitoring for an indication that the alert has been responded to by a user and, if the pneumatic device is ready to use, automatically starting the therapy protocol.

According to a fifth aspect of the present disclosure, a therapy system comprises a patient support apparatus and a pneumatic therapy device. The patient support apparatus includes a frame, a patient support surface supported on the frame, a user interface, and an air system supported on the frame. The air system includes a source of pressurized air, an outlet coupled to the source of pressurized air, and an air system controller in communication with the user interface, the source of pressurized air, and the outlet. The air system controller includes processor, and a memory device. The therapy system also includes a port removeably pneumatically coupling the pneumatic therapy device and the outlet. The memory device includes instructions, that, when executed by the processor, causes the air system controller to determine that a patient is supported on the patient support apparatus and that a therapy protocol has been entered for the patient associated with the patient support apparatus to thereby initiate operation of the pneumatic therapy system to provide the therapy protocol.

According to some embodiments of the fifth aspect, the patient support apparatus may further includes a plurality of sensors coupled to the frame and in communication with the air system controller.

According to some embodiments of the fifth aspect, the memory device may include instructions, that, when executed by the processor, causes the air system controller to communicate with the plurality of sensors to determine the weight of an occupant positioned on the patient support apparatus and correlate the weight of the occupant to an amount of pressure applied thereon by the pneumatic therapy device.

According to some embodiments of the fifth aspect, the air system controller may further determine the initiation of therapy and pressure changes within the sleeve and compare the pressure changes to a pre-programmed pressure threshold programmed within the memory device.

According to some embodiments of the fifth aspect, the therapy system may further include an electronic medical records system, and a communications engine in communication with the patient support apparatus and the electronic medical records system. The communications engine identifies and associates an occupant located in the patient support apparatus to the patient support apparatus. The communications engine further transmits a command to the patient support apparatus indicating and automatically starting a pneumatic therapy protocol associated with the occupant located in the patient support apparatus.

According to some embodiments of the fifth aspect, the communications engine may be in further communication with a nurses' station and conveys the pneumatic therapy protocol to the nurses' station for display.

According to some embodiments of the fifth aspect, the air system controller may update the user interface to provide access to the air system controller to control operation of the pneumatic therapy device from the user interface.

According to some embodiments of the fifth aspect, the user interface may be in communication with the pneumatic therapy device and displays pneumatic therapy device controls, pneumatic therapy parameters, and a current status of the pneumatic therapy device.

According to some embodiments of the fifth aspect, the pneumatic therapy device may include an at least one sleeve engages an occupant positioned in the patient support apparatus, and an at least one hose having a first end, and a second end spaced apart from the first end. The at least one hose may removeably couple to the sleeve at the first end of the at least one hose and to the coupler at the second end of the at least one hose, the at least one hose directs a pressurized airstream from the air system to the sleeve.

According to some embodiments of the fifth aspect, the pneumatic therapy device may further include a plurality of sensors coupled thereto to determine when the at least one sleeve is removeably coupled to the occupant.

According to some embodiments of the fifth aspect, the at least one sleeve and the at least one hose may couple to the patient support apparatus at a smart connecter, the smart connector determines when the at least one sleeve is coupled to the occupant and the outlet of the air system by measuring and identifying any change in the air volume within the at least one hose.

According to some embodiments of the fifth aspect, the frame may include a base; a lift mechanism coupled to the base; and an upper frame assembly coupled to the lift mechanism. The upper frame assembly may be formed to include a foot end, and a head end spaced apart from the foot end.

According to some embodiments of the fifth aspect, the foot end of the upper frame may be formed to include an indicator projecting a plurality of display icons conveying the status of the pneumatic therapy device onto a floor of a patient room.

According to some embodiments of the fifth aspect, the indicator may be controlled through the user interface of the patient support apparatus.

According to some embodiments of the fifth aspect, the plurality of display icons may be dynamic.

According to some embodiments of the fifth aspect, the upper frame assembly and base may include an at least one nightlight formed to illuminate an at least one zone of a patient room in response to an input in the user interface.

According to some embodiments of the fifth aspect, the frame may further include a pair of siderails coupled to the upper frame assembly and formed to include an at least one night light.

According to some embodiments of the fifth aspect, the therapy system may further include a data management system in communication with the patient support apparatus and receives a plurality of measured data from the patient support apparatus and communicates the plurality of measured data to a remote caregiver controller.

According to some embodiments of the fifth aspect, the data management system ma further compare the plurality of measured data to a pre-programmed plurality of thresholds and communicates and alert to the remote caregiver controller.

According to some embodiments of the fifth aspect, the air system controller may update the user interface to inform a caregiver of an error location and instructions on how to fix the error.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The brief description particularly refers to the accompanying figures in which.

DETAILED DESCRIPTION

Figure 1:
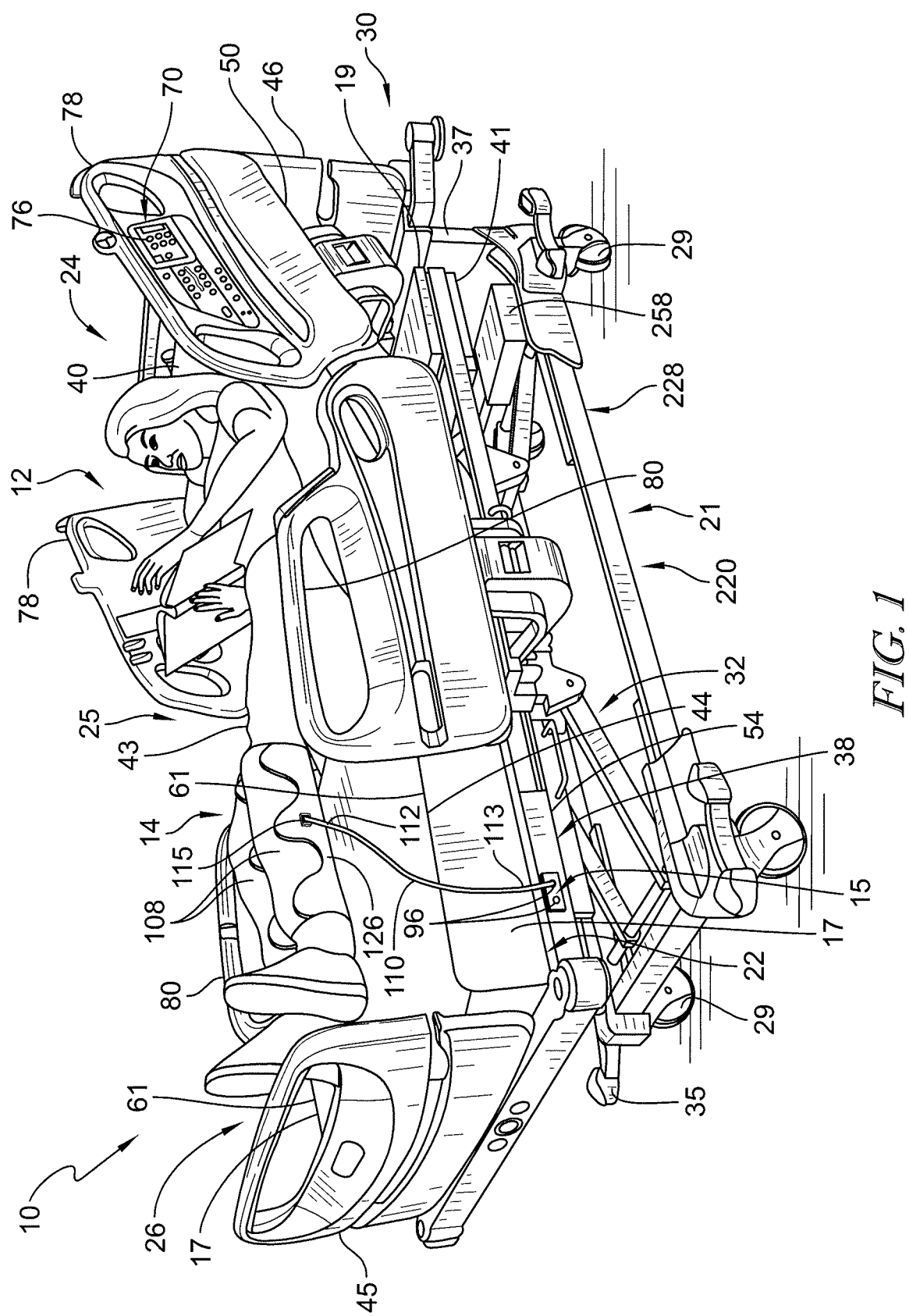
FIG. 1 is a perspective view of a patient support apparatus illustratively embodied as a hospital bed with a therapy system and showing a patient lying on the bed with compression sleeves positioned on the patient's lower limbs and further showing a foot section of a frame of the hospital bed having ports for coupling a conduit thereto, the conduit extending between the port and the compression sleeve to guide pressurized fluid between the patient support and the compression sleeves.
Figure 2:
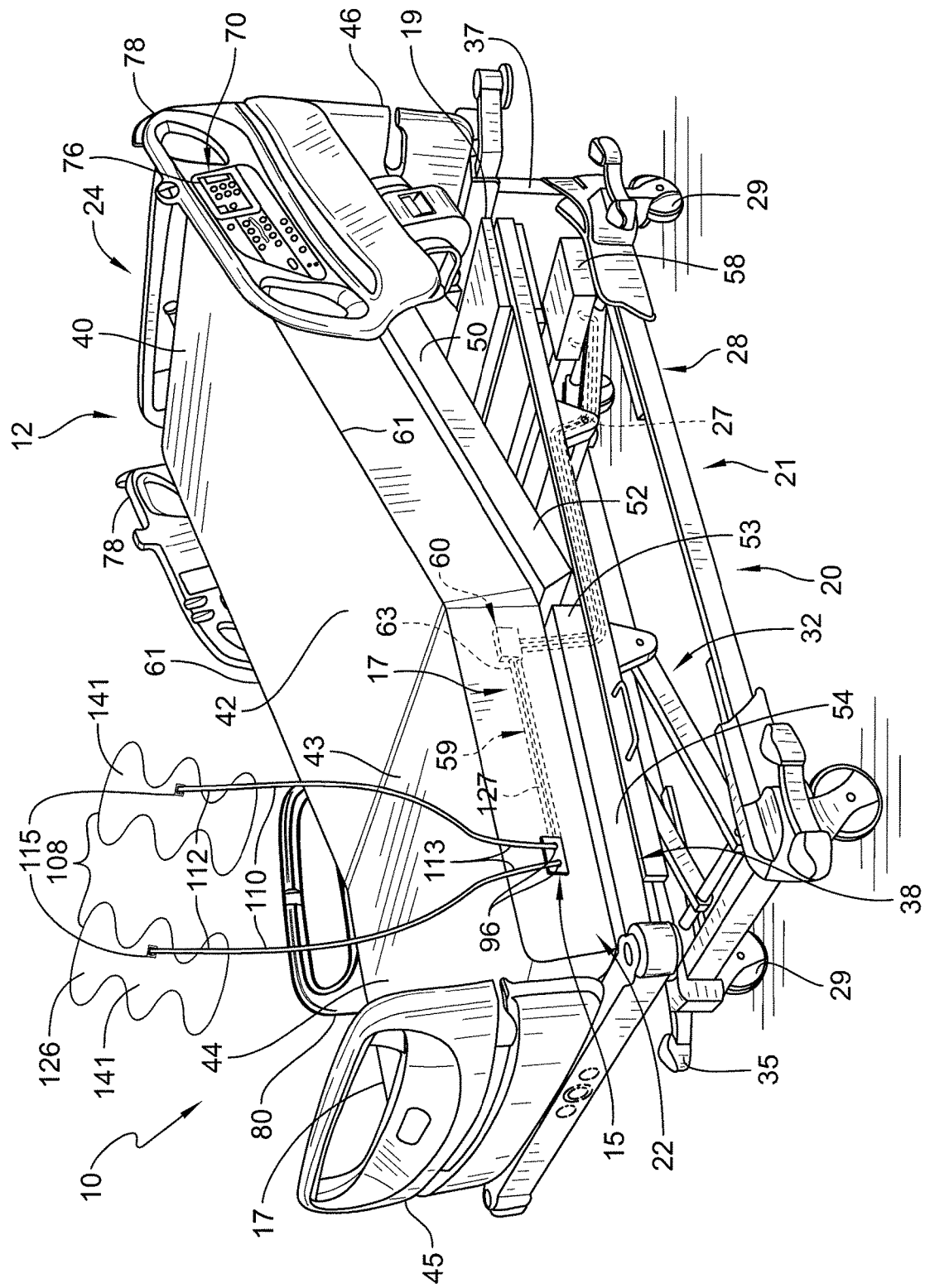
FIG. 2 is a perspective view of the patient support apparatus of FIG. 1 showing a portion of the air system of the bed coupled to the frame of the patient support apparatus and in communication with the conduit and compression sleeve(s) (together forming a pneumatic therapy device) coupled thereto.

In one embodiment of a therapy system 10, the system 10 includes a patient support apparatus 12 and a pneumatic therapy device 14 configured to couple to the patient support apparatus 12. The patient support apparatus 12, illustratively embodied as a hospital 12, includes a patient support structure 21 such as a frame 21 that supports a surface or mattress 22 as shown in FIGS. 1 and 2. While the patient support apparatus 12 is embodied as a hospital bed 12, this disclosure is applicable to other types of patient support apparatuses, including other types of beds, surgical tables, examination tables, stretchers, and the like. As will be described below in further detail, a main controller 18 (shown in FIG. 3) of patient support apparatus 12 is operable to control operation of pneumatic therapy device 14 using an air system 20 of patient support apparatus 12.

Pneumatic therapy device 14 is illustratively embodied as a sequential compression device assembly (SCD assembly) 14, as shown in FIGS. 1 and 2, although a variety of other pneumatic therapy devices known in the art may be used in addition to/in place of SCD assembly 14. As such, pneumatic therapy device and SCD assembly 14 are used interchangeably throughout the application. Pneumatic therapy device 14 disclosed herein utilizes an air source 58 of air system 20 coupled to patient support apparatus 12, shown diagrammatically in FIGS. 3 and 4, and is formed to include one or more compression sleeves 108 that are placed upon a patient's limbs as shown, for example, in FIG. 1. Air source, air supply, and source for pressurized air are used interchangeably throughout the application. In some embodiments, sleeves 108 are embodied as wraps that are sized to wrap about a patient's calves, thighs, and/or feet. Combination sleeves (not shown) that attach to a patient's calves and feet or that attach to a patient's calves and thighs or that attach to a patient's feet, calves and thighs are within the scope of this disclosure. Upper limb sleeves (not shown) removeably coupleable to a patient's arms and/or torso are also within the scope of this disclosure. However, sleeves 108 that attach to the patient's lower limbs are the ones that are most commonly used in sequential compression device assembly 14, particularly, for the prevention of deep vein thrombosis (DVT).

The SCD assemblies 14 disclosed herein are sometimes referred to as limb compression devices, intermittent compression devices (ICDs), DVT prevention systems, or the like. Thus, these terms and variants thereof are used interchangeably herein to cover all types of devices and systems that have compression sleeves with one or more inflatable and deflatable chambers that are controlled pneumatically by delivery and removal of air or other gas from a set of pneumatic components that are contained within patient support apparatus 12.

Referring to FIGS. 1 and 2, frame 21 of patient support apparatus 12 includes a lower frame or base 28, an upper frame assembly 30, and a lift system 32 coupling upper frame assembly 30 to base 28. Lift system 32 is operable to raise, lower, and tilt upper frame assembly 30 relative to base 28. Patient support apparatus 12 has a head end 24 and a foot end 26 spaced apart from each other with a body section 25 extending therebetween. Patient support apparatus 12 further includes a footboard 45 coupled to patient support apparatus 12 at foot end 26, a headboard 46 coupled to patient support apparatus 12 at head end 24, and a pair of sides 17 spaced apart from each other and extending laterally from foot end 26 to head end 24 of patient support apparatus 12. Headboard 46 is coupled to an upstanding portion 37 of base 28. Footboard 45 is removeably coupled to an extendable and retractable portion 47 of a foot section 54 of a patient support deck 38 of upper frame assembly 30. In other embodiments, footboard 45 is coupled to a foot end 39 of upper frame assembly 30. Illustratively, base 28 includes a plurality of wheels or casters 29 that roll along a floor as patient support apparatus 12 is moved from one location to another. A set of foot pedals 35 are coupled to base 28 and are used to brake and release casters 29 as is known in the art.

Illustrative patient support apparatus 12 has four siderail assemblies coupled to upper frame assembly 30 as shown in FIG. 1. The four siderail assemblies include a pair of head siderail assemblies 78 (sometimes referred to as head rails) and a pair of foot siderail assemblies 80 (sometimes referred to as foot rails). Each of the siderail assemblies 78, 80 is movable between a raised position, as shown in FIG. 1, and a lowered position (not shown but well-known to those skilled in the art). Siderail assemblies 78, 80 are sometimes referred to herein as siderails 78, 80.

Upper frame assembly 30 includes a patient support deck 38 that supports mattress 22. Patient support deck 38 is situated over an upper frame 19 of upper frame assembly 30. Mattress 22 includes a head section 40, a seat section 42, a thigh section 43, and a foot section 44 in the illustrative example as shown in FIGS. 1 and 2. Patient support deck 38 is formed to include a head section 50, a seat section 52, a thigh section 53, and a foot section 54 such that respective mattress sections 40, 42, 43, 44 are positioned thereon. Mattress sections 40, 42, 43, 44 are each movable relative to upper frame 19. For example, head section 40 pivotably raises and lowers relative to seat section 42 whereas foot section 54 pivotably raises and lowers relative to thigh section 43. Additionally, thigh section 53 articulates relative to seat section 42.

Mattress 22 further includes a pair of edges 61 wherein each of the pair of edges 61 is spaced apart from each other with respective section 40, 42, 43, 44 extending therebetween. In the illustrative embodiment, thigh section 43 and/or foot section 44 is configured to support SCD assembly 14 when independent of the patient as well as when coupled thereto. As will be discussed below, in some embodiments, thigh section 43 and/or foot section 44 may be formed to integrally include SCD assembly 14 and/or be configured to store SCD assembly 14 therein when not in use, when patient is ambulatory, and/or to avoid SCD assembly 14 from contacting a floor of a hospital/care center.

Figure 3:
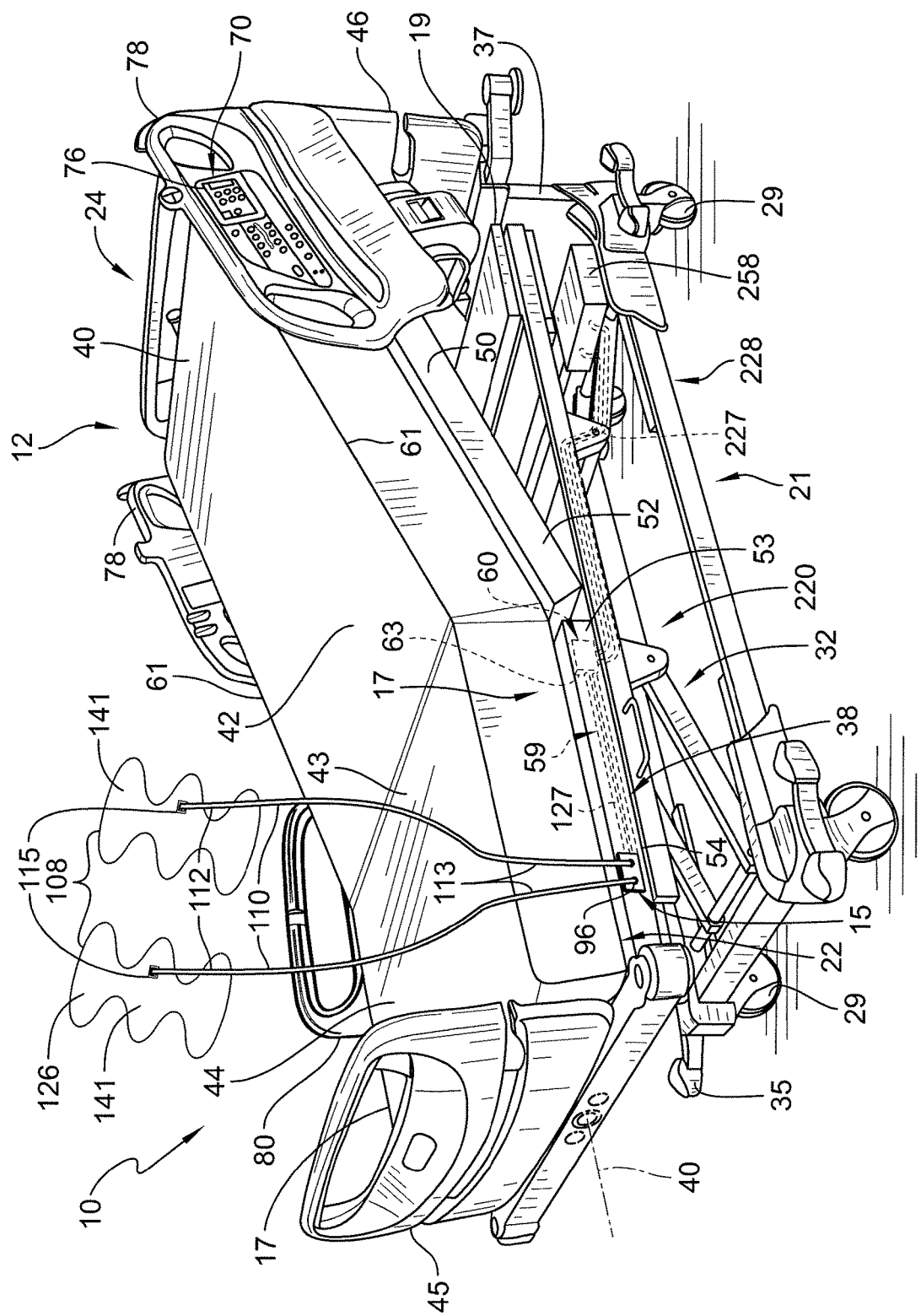
FIG. 3 is a perspective view of another embodiment similar to FIG. 1, the embodiment of FIG. 3 having compression sleeves coupled to the bed and further showing a foot section of the frame of the hospital bed having ports for coupling a conduit thereto, the conduit extending between the port and the compression sleeve to guide pressurized fluid between the patient support apparatus and the compression sleeves.
Figure 4:
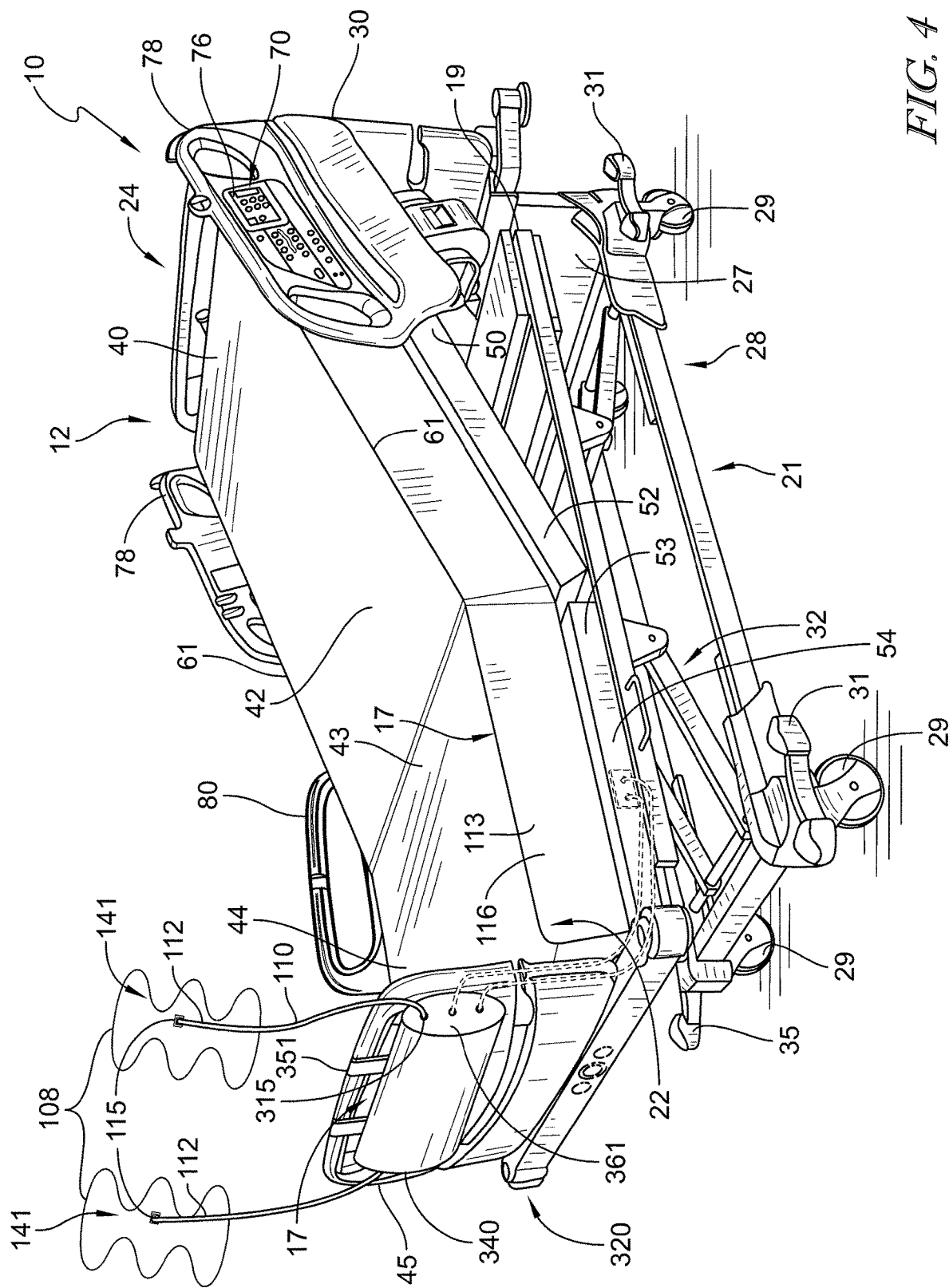
FIG. 4 is a perspective view of another embodiment similar to FIG. 1, the embodiment of FIG. 4 including an air source located in a housing removeably coupled to a footboard of the bed, the air source is configured to couple to the conduits and may further be configured to couple to the bed for power.

Referring to FIGS. 3 and 4, when in use, SCD assembly 14 is configured to communicate with main controller 18 electrically coupled to air system 20 and a user interface 70. Main controller 18 may be formed to include various circuit boards, electronics modules, and the like that are electrically and communicatively interconnected. Main controller 18 includes one or more microprocessors or microcontrollers 72 that execute software to perform the various bed control functions and algorithms along with compression device control functions and algorithms as described herein. Thus, main controller 18 also includes memory 74 for storing software, variables, calculated values, and the like as is known in the art.

Figure 6:
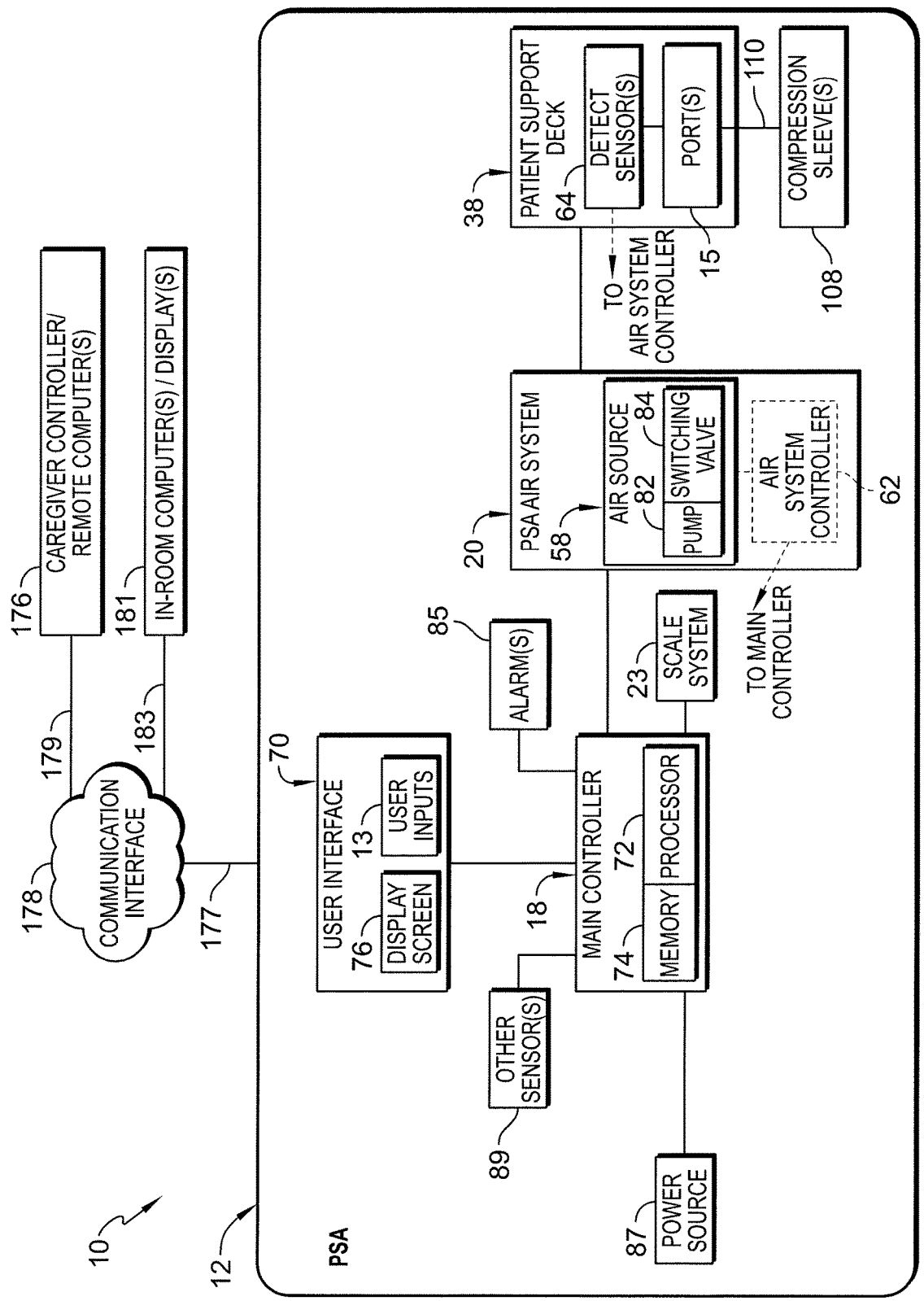
FIG. 6 is a block diagram showing the electric and communication components of the bed of FIG. 1 and showing the compression sleeve(s) and conduit in communication with an air system controller configured to communicate with a main controller of the patient support apparatus.

As shown diagrammatically in FIG. 6, main controller 18 includes a processor 72 and a memory device 74 that stores instructions and/or algorithms used by processor 72. Processor 72 executes the instructions and algorithms stored in memory 74 to perform the various bed control functions and algorithms along with SCD assembly 14 functions and algorithms described herein.

Main controller 18 is further configured to be in communication with user interface 70. User interface 70 is configured to receive user inputs by the caregiver and/or patient, to communicate such input signals to main controller 18 of patient support apparatus 12 to control the operation of air system 20 and SCD assembly 14 of patient support apparatus 12, and to control the operation of other functions of patient support apparatus 12. User interface 70 is further configured to provide access to air system controller 62 to control operation of SCD assembly 14 from user interface 70. User interface 70 may be formed as a graphical user input (GUI) or display screen 76 coupled to a respective siderail 78 as shown in FIGS. 1 and 2. Display screen 76 is coupled to main controller 18 as shown diagrammatically in FIG. 6. In some embodiments, two GUI's 76 are provided and are coupled to head siderails 78. Alternatively or additionally, one or more GUI's are coupled to foot siderails 80 and/or to one or both of the headboard 46 and footboard 45. Alternatively or additionally, GUI 76 is provided on a hand-held device such as a tablet, phone, pod or pendant that communicates via a wired or wireless connection with main controller 18.

As such, main controller 18 is configured to act on information provided by user interface 70 to control air system 20 based on inputs from a user. For example, user interface 70 includes a user input device (not shown) that is indicative of when a user wishes to actuate therapy of SCD assembly 14. The user input device corresponds to sequential compression of SCD assembly 14. Similarly, the user input device provides a signal to main controller 18 that therapy provided by SCD assembly 14 is to be halted when the user input device provides a signal indicative of a user's desire to stop sequential compression of SCD assembly 14. As such, user input devices may signal/indicate that the sequential compression of the respective SCD assembly 14 is to be actuated and/or ceased.

In some embodiments, main controller 18 of patient support apparatus 12 communicates with a caregiver controller/remote computer device 176 via a communication infrastructure 178 such as a wired network of a healthcare facility in which patient support apparatus 12 is located and/or via communications links 177, 179 as shown diagrammatically in FIG. 6. Infrastructure 178 may be operated according to, for example, wired and/or a wireless links. Caregiver controller 176 is sometimes simply referred to as a "computer" or a "server" herein. In some embodiments, main controller 18 of patient support apparatus 12 communicates with one or more in-room computers or displays 181 via communication infrastructure 178 and communications link 183. In some embodiments, display 181 is an in-room station or a nurse call system.

Remote computer 176 may be part of a bed data system, for example. Alternatively or additionally, it is within the scope of this disclosure for circuitry (not shown) of patient support apparatus 12 to communicate with other computers 176 and/or servers such as those included as part of an electronic medical records (EMR) system, a nurse call system, a physician ordering system, an admission/discharge/transfer (ADT) system, or some other system used in a healthcare facility in other embodiments, although this need not be the case.

In the illustrative embodiment, patient support apparatus 12 has a communication interface which provides bidirectional communication via link 177 with infrastructure 178 which, in turn, communicates bidirectionally with computers 176, 181 via links 179, 183 respectively as shown in FIG. 6. Link 177 is a wired communication link in some embodiments and is a wireless communications link in other embodiments. Furthermore, communications links 179, 183 each comprises one or more wired links and/or wireless links as well, according to this disclosure. Remote computer 176 may be part of a bed data system, for example. Alternatively or additionally, it is within the scope of this disclosure for the circuitry of patient support apparatus 12 to communicate with other computers 176 and/or servers such as those included as part of the EMR system, a nurse call system, a physician ordering system, an admission/discharge/transfer (ADT) system, or some other system used in a healthcare facility in other embodiments, although this need not be the case.

Still referring to FIG. 6, main controller 18 is in communication with a scale system 23 coupled to frame 21 that may be operable to determine a weight of the patient positioned on patient support apparatus 12. Main controller 18 may vary an operating parameter of therapy system 10 depending upon the weight of the patient sensed by scale system 23. Scale system 23, using load cells, is used to detect the weight of a patient positioned on the patient support apparatus 12, movement of the patient on patient support apparatus 12, and/or the exit of the patient from patient support apparatus 12. Other sensors may be used in conjunction with or as an alternative to the load cells of the scale system 23, including, for example, force sensitive resistors (FSRs) that are placed beneath the mattress 22 of the patient support apparatus 12 on the patient support deck 38.

As shown in FIG. 6, patient support apparatus 12 has one or more alarms 85. Such alarms 85 may be one or more audible alarms and/or visual alarms coupled to the circuitry. Audible alarms 85 include, for example, a speaker, piezoelectric buzzer, or the like. The circuitry controls audible alarms 85 to sound in response to various alarm conditions detected. Visual alarms 85 include, for example, one or more alert lights that are provided on frame 21 of patient support apparatus 12 and that are activated in different ways to indicate the conditions of patient support apparatus 12. For example, when no alerts or alarms exist, the lights are activated to shine green. When an alert or alarm occurs, including a bed exit alarm, lights are activated to shine red or amber and, in some embodiments, to blink. Other visuals alarms that may be used in addition to, or instead of, such alert lights include changing a background color of graphical display screen 76 and/or displaying an iconic or textual alarm message on display screen 76 and may even include IV pole mounted or wall mounted devices such as lights and/or graphical display screens.

It should be understood that FIG. 6 is diagrammatic in nature and that various portions of patient support apparatus 12 and the circuitry thereof is not depicted. However, a power source block 87 is intended to represent an onboard battery of patient support apparatus 12 and an AC power cord of patient support apparatus 12 as well as the associated power handling circuitry. Also, the block representing other sensors 89 represents all other sensors of patient support apparatus 12 such as one or more sensors 64 used to sense whether a caster braking system of patient support apparatus 12 is in a braked or released position and/or sensors 89 used to detect whether each of the siderail assemblies 78, 80 is raised or lowered, or other sensors as known in the art.

As discussed above, main controller 18 includes a processor 72 and a memory device 74 that stores instructions used by processor 72 as shown in FIGS. 3 and 4. Processor 72 may further consider information gathered from sensors 64, air system controller 62, and SCD assembly 14 to determine when to actuate, adjust, or cease the sequential compression. Illustratively, such sensors 64 are embodied as pressure sensors 64 although it may be embodied as other sensors known in the art used either alone or in combination with pressure sensors 64.

Further, memory device 74 may be pre-programmed to alert the caregiver upon exceeding a predetermined threshold so to avoid patient discomfort, pressure necrosis, and/or loss of capillary integrity leading to edema and increased compartmental pressures. To explain, memory device 74 may be configured to alert the caregiver of a pressure of SCD assembly 14 which exceeds a predetermined threshold pre-programmed therein.

Such a predetermined threshold of pressure may be based on the patient's vitals, medical history, desired outcome of pneumatic therapy (i.e.: sequential compression therapy via SCD assembly 14), as well as other data measurements by sensors 64. Therefore, it is desirable to identify the sequential compression threshold of each patient and avoid reaching such a threshold to avoid patient discomfort, pressure necrosis, and other associated complications.

Figure 5:
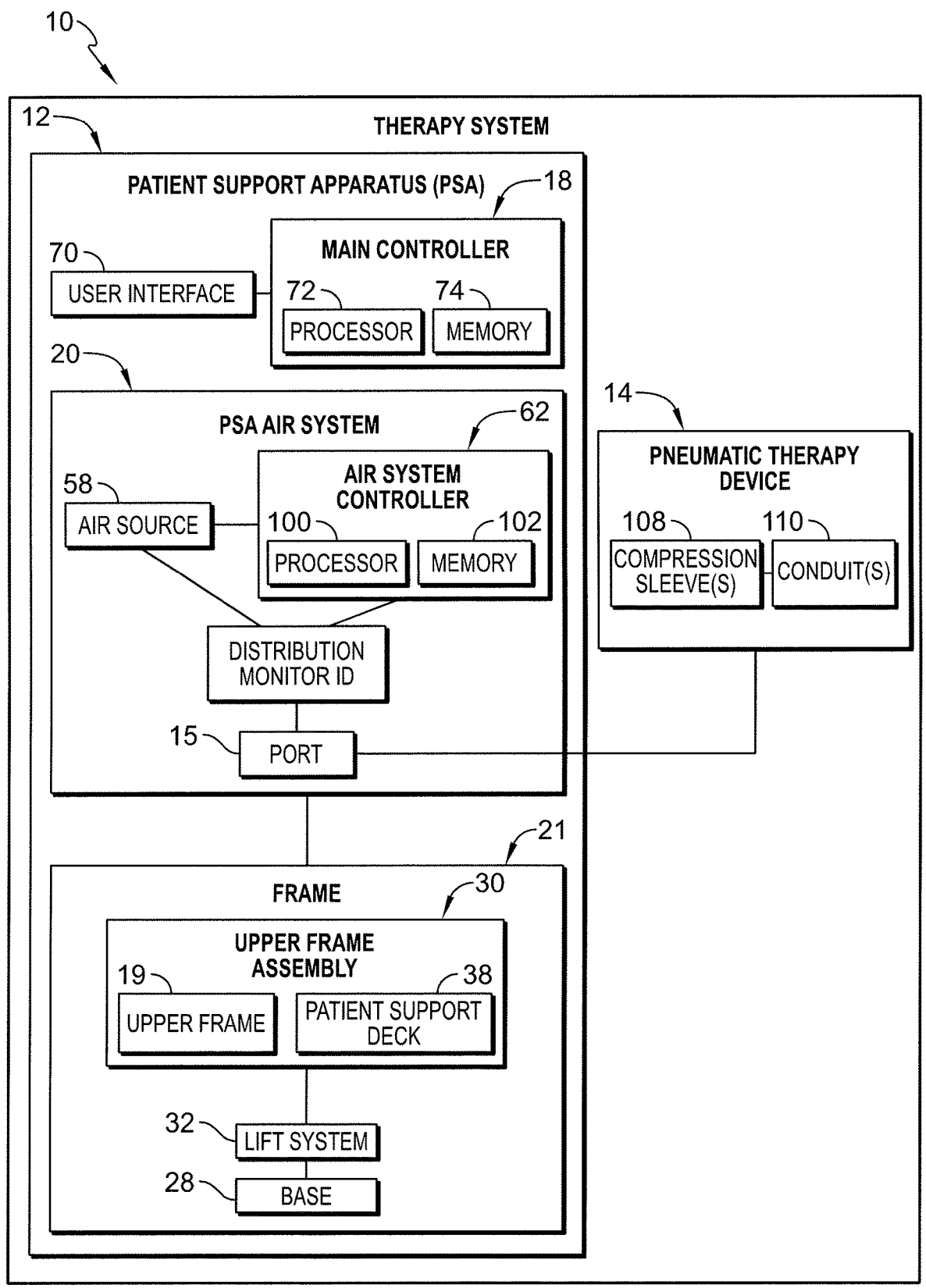
FIG. 5 is a block diagram showing the pneumatic components of the bed of FIG. 1 and showing the pneumatic therapy device of FIG. 2 in communication with the air system of the patient support apparatus.

As mentioned previously, the operation of SCD assembly 14 is controlled by main controller 18 in communication with air system 20. Main controller 18 is configured to communicate with an air source 58, 258 and a respective distribution manifold/outlet 60, 260. While only air source 58 is shown in FIG. 5, it should be understood that the operation described herein will be equally applicable to other embodiments using similar structures.

In other embodiments, as shown in FIG. 2, portions of air system 20 are illustratively located within mattress 22 and is configured to supply and direct a pressured air stream to SCD assembly 14. Air system 20 includes a source of pressurized air 58, a distribution manifold 60, and an air system controller 62. Source of pressurized air 58 is configured to generate and communicate a pressurized air stream to SCD assembly 14 through distribution manifold 60 located in mattress 22 and a plurality of tubes 27 extending therebetween. A plurality of air hoses 59 are coupled to distribution manifold 60 and extend between distribution manifold 60 and edge 61 of mattress 22 terminating in a port 15. Plurality of tubes 27, distribution manifold 60, and plurality of air hoses 59 cooperate to guide the pressurized air stream from source of pressurized air 58 to SCD assembly 14. Distribution manifold 60 is formed to include a plurality of valves 63 and a plurality of pressure sensors 64 and is configured to adjust the pressure of the air from the source of air 58 before it enters pneumatic therapy device 14. Air system controller 62 is in communication with main controller 18, source of pressurized air 58, and distribution manifold 60 and is operable to detect connection of SCD assembly 14 to port 15, communicate detection of connection to main controller 18, and initiate operation of therapy system 10 in response to the communication. The detection of SCD assembly 14 may be accomplished by an at least one pressure/attachment sensor 64 configured to identify attachment of SCD assembly 14 to port 15.

In other embodiments of patient support apparatus 12, as shown in FIGS. 1 and 3, air system 220 is illustratively coupled to frame 21 underneath a head end 41 of upper frame assembly 30 and is configured to supply and direct a pressured air stream to SCD assembly 14. Air system 220 includes a source of pressurized air 258, a distribution manifold 260, and an air system controller 62. Source of pressurized air 258 is configured to generate and communicate a pressurized air stream to SCD assembly 14 through distribution manifold 260 coupled to frame 21 and a plurality of tubes 227 extending between the source of pressurized air 258 and the distribution manifold 260. A plurality of air hoses 259 are coupled to distribution manifold 260 and extend between distribution manifold and edge 231 of patient support deck 238 terminating in a port 15. Plurality of tubes 227, distribution manifold 260, and plurality of air hoses 259 cooperate to guide the pressurized air stream from source of pressurized air 258 to SCD assembly 14. Distribution manifold 260 is formed to include a plurality of valves 63 and a plurality of pressure sensors 64 and is configured to adjust the pressure of the air from the source of air 258 before it enters pneumatic therapy device 14. Air system controller 62 is in communication with main controller 18, source of pressurized air 258, and distribution manifold 260 and is operable to detect connection of SCD assembly 14 to port 15, communicate detection of connection to main controller 18, and initiate operation of therapy system 10 in response to the communication. The detection of SCD assembly 14 may be accomplished by an at least one pressure/attachment sensor 64 configured to identify attachment of SCD assembly 14 to port 15.

In other embodiments of patient support apparatus 12, as shown in FIG. 4, air system 320 is formed independent of patient support apparatus 12 and is removeably coupled to footboard 45 of patient support apparatus 12 and is configured to supply and direct a pressured air stream to SCD assembly 14 coupled thereto. Air system 320 includes a source of pressurized air (not shown), a distribution manifold (not shown), and an air system controller 62. Source of pressurized air and distribution manifold are located in a housing 340 and configured to generate and guide a pressurized air stream a port 15 formed in a side 361 of the housing 340. Housing 340 is formed to removeably couple to footboard 345 using clips 351, hooks 351, or other mechanisms known in the art. Air system 320 is further configured to couple to footboard 345 for power such that the source of air located in housing 340 draws power from patient support apparatus 12.

In some embodiments, the air system 320 further includes a plurality of tubes shown in phantom (not shown) extending between the housing 340 and a port coupled to the frame of the patient support apparatus 12. The plurality of tubes cooperate to guide the pressurized air stream from source of pressurized air from the patient support apparatus 12 to the air system 320. In such an embodiment, the air system 320 does not have an independent source of pressurized air, but receives pressurized air from the patient support apparatus 12 and controls the operation of the sleeves 108. In some embodiments, the air system 320 may be independent of the main controller 18 of the patient support apparatus 12. In other embodiments, the air system 320 may be in electrical communication with the main controller 18 and cooperate with the user interface 76 to allow control of the air system 320 from the user interface 76. The detection of SCD assembly 14 may be accomplished by an at least one pressure/attachment sensor 64 configured to identify attachment of SCD assembly 14 to port 15.

Source of pressurized air 58, 258 is in communication with main controller 18 and air system controller 62 and coupled to distribution manifold 60, 260 as shown in FIGS. 2, 3, and 4. In FIGS. 1-3, source of pressurized air 58, 258 is illustratively embodied as a compressor of patient support apparatus 12 such that air system 20, 220 shares air source 58, 258 with patient support apparatus 12 as well as with other therapy systems 14 coupled thereto. In utilizing a single source of pressurized air 58, 258 for functions of patient support apparatus 12 and air system 20, 220, therapy system 10 reduces the clutter of a second, distinct source of pressurized air commonly associated with SCD assemblies 14 and configured to operate solely with SCD assembly 14 and/or other modular therapies. As such, in some contemplated embodiments, wherein mattress 22 is an air mattress that contains one or more air bladders or layers (not shown), air system 20, 220 may be configured to control inflation and deflation of the various air bladders or cells and/or layers of air mattress 22 as well as SCD assembly 14. Source of pressurized air 58, 258 may be embodied as a fan, a blower, or any other source as is known in the art configured to provide pressurized.

In the embodiments shown in FIG. 1-3, source of pressurized air 58, 258 is coupled to frame 21 at base 28 and is further coupled to a plurality of tubes 27, 227 such that the pressurized air produced in source 58, 258 may be guided into air hoses 59, 259. In some embodiments, plurality of tubes 27, 227 may be those already coupled to patient support apparatus 12 and extending between the bed blower/compressor 58, 258 and the patient support apparatus 12. In other embodiments, the plurality of tubes 27, 227 extends from the air source 58, 258, up lift system 32, along upper frame assembly 30, and terminates at distribution manifold 60, 260. From distribution manifold 60, 260, air hoses 59, 259 are routed to port 15 formed in each of the pair of sides 61 of mattress 22 and/or edges 231 of deck 238. Illustratively, at least two air hoses 59, 259 are routed to each of the pair of edges/sides 231, 61, terminate at a port 15, 215 formed in each of the edges/sides 231, 61. Illustratively, a port 15 is formed in the foot section 44 of each side 61 of mattress 22 and/or the foot section 54 of each edge 231 of deck 238. Port 15 is configured to couple to SCD assembly 14 and, thereby, guide pressurized air into SCD assembly 14 during therapy. Illustratively, port 15 is formed to include a plurality of apertures/valves 16. Each aperture/valve 16 is configured to couple to a single SCD assembly/therapy module 14 such that each port 15 is configured to couple to multiple SCD assemblies 14/therapy modules 14.

As shown in FIG. 6, source of pressurized air 58, 258 includes a pump 82 and a switching valve 84. Pump 82 is coupled to switching valve 84 and configured to draw ambient atmospheric air into air source 58, 258, and exhaust air into the atmosphere. Switching valve 84 is exposed to the atmosphere and configured to either provide for or block the air into and out of air source 58, 258. Pump 82 includes an inlet (not shown) and an outlet (not shown) coupled to switching valve 84 and is configured to cooperate with switching valve 84 is create a flow path for the air. Switching valve 84 includes a plurality of outlets (not shown) coupled to the inlet of pump 82 and a second inlet (not shown) coupled to the outlet of pump 82. At least one outlet of switching valve 84 is open to the atmosphere to provide the flow path for drawing air into air source 58, 258 or exhausting air to the atmosphere depending on the position of switching valve 84.

Distribution manifold 60, 260, 360 (not shown) is operable to close the plurality of valves 63 to maintain the pressure in SCD assembly 14. Illustratively, valves 63 are embodied as solenoid valves. Manifold 60, 260 may also selectively control venting of the SCD assembly 14 to an exhaust (not shown). Illustratively, distribution manifold 60, 260 guides pressurized air stream towards port 15. Port 15 is configured to couple to a single SCD assembly/therapy module 14 such that each port 15 is configured to couple to multiple SCD assemblies 14/therapy modules 14. Illustratively, each port 15 is configured to couple to two SCD assemblies 14 such that each port 15 is configured to operate independently of the other. In some embodiments, additional ports 15 are formed in patient support apparatus 12 and configured to couple to additional SCD assemblies and/or other therapy devices 14. Distribution manifold 60, 260 is in communication with air system controller 62 and configured to operate in response to commands from air system controller 62 and/or main controller 18.

As such, upon receiving an input from user interface 70, main controller 18 communicates the appropriate signal(s) to air system controller 62 to control air system 20. Therefore, when a function is requested by main controller 18, air system controller 62 is configured to energize the appropriate valve of manifold 60, 260 and set the appropriate pulse width modulation for source of pressurized air 58, 258. Illustratively, ambient, environmental air enters air system 20, 220 through an inlet air filter (not shown). The ambient air travels into source of pressurized air 58 through an inlet orifice (not shown). Source of pressurized air 58, 258 then pushes the pressurized air produced therein through a discharge hose (not shown) into an inlet (not shown) of manifold 60, 260 through manifold 60, 260 and plurality of tubes 27, 227 coupled thereto, and to SCD assembly 14 and/or appropriate bladders positioned within mattress 22, 322.

Illustratively, pressurized air is guided into conduit 110 of SCD assembly 14 through port 15. Conduit 110 guides the pressurized air into compression sleeve 108 via a pneumatic connector 115 formed in an outer surface 141 of sleeve 108. Illustratively, each sleeve 108 is formed to include a pressure tap (not shown) in communication with air system 20. The pressure taps are routed to manifold 60 and coupled to a plurality of pressure sensors 64 through sense lines through air system controller 62 for feedback of pressure levels within SCD assembly 14. For example, if pressure in sleeve(s) 108 exceeds a threshold pre-programmed in main controller 18, pressure sensors 64 sense the sleeve(s)' 108 pressure, provide feedback to main controller 18, and the main controller 18 communicates with air system controller 62 to adjust the pressure of sleeve(s) 108 accordingly. The aforementioned system is closed-loop and feedback dependent.

Illustratively, sensors of sensor block 89, such as, for example, Hall-effect sensors, RFID sensors, near field communication (NFC) sensors, pressure sensors, or the like, are configured to sense tokens (e.g., magnets, RFID tags, NFC tags, etc.). Illustratively, the type/style of sleeve 108 is sensed by sensors 89 and communicated to main controller 18 which, in turn, communicates the sleeve 108 type information to the circuitry for ultimate display on GUI 76 in connection with the compression device control screens. Illustratively, pressure sensors 64 are configured to identify the presence and absence of conduit 110 and, in response, automatically begin, halt, or adjust therapy, respectively, which is discussed in further detail below.

The aforementioned sensed pressure corresponds to the output of source for pressurized air 58, 258. As such, air system controller 62 is configured to regulate the speed of source of pressurized air 58, 258 in correlation to pressure. For example, if a pre-programmed threshold requires a particular discharge from source of pressurized air 58, 258 for function of SCD assembly 14, then main controller 18 is configured to communicate to air system controller 62 so that the appropriate pulse width modulation settings are fixed so to establish the correct pressure and flow output from source of pressurized air 58, 258.

Air system controller 62 includes a processor 100 and a memory device 102 which stores instructions used by processor 100 as shown in FIG. 5. In some embodiments, processor 100 may consider information gathered from pressure sensors 64 and/or SCD assembly 14 to determine when to provide pressure to SCD assembly 14 such that sequential compression may occur. As discussed above, in some embodiments, main controller 18 is in communication with air system controller 62 such that upon reaching a predetermined pressure threshold, a signal is sent first from pressure sensors 64 to main controller 18 and then communicated to air system controller 62. In some embodiments, air system controller 62 itself is pre-programmed to identify pressure exceeding a preprogrammed threshold and is further configured to convey such information to main controller 18. Illustratively, air system controller 62 and main controller 18 are configured to cooperate to alert the caregiver when the pressure of SCD assembly 14 exceeds the pre-programmed threshold.

As discussed above, SCD assembly 14 is configured to provide sequential compression therapy to a patient positioned on patient support apparatus 12 as shown in FIG. 1. SCD assembly 14 is removeably coupled to distribution manifold 60 and is configured to contain the pressurized air stream such that the pressure thereof may be applied to the patient via SCD assembly 14. SCD assembly 14 includes at least one compression sleeve 108 and at least one conduit 110 having a first end 112 removeably coupled to compression sleeve 108 and a second end 113 removeably coupled to port 15. In the illustrative embodiment, sleeve 108 is formed to fit a patient's lower leg. In other embodiments, the sleeve 108 may be formed to fit a patient's foot, calf, thigh, or some combination thereof. Conduit 110 is configured to extend between sleeve 108 and distribution manifold 60 such that the pressurized air stream formed by source of pressurized air 58 is directed from source 58 through distribution manifold 60 and further through conduit 110 until reaching sleeve 108. As such, when sleeve 108 is positioned on a lower extremity of the patient, SCD assembly 14 is configured to provide each lower extremity of the patient with therapy independent of the other. Further, main controller 18 may be configured to selectively inflate a first compression sleeve 108 independent of a second compression sleeve 108 such that the second compression sleeve 108 remains uninflated throughout the duration of therapy. Illustratively, each sleeve 108 has a respective conduit 110 coupled thereto and is independent of the other. In some embodiments, a single conduit 110 is shared between multiple sleeves 108.

As such, sleeves 108 are configured to adjust the amount of compression applied to the patient in response to instructions from main controller 18 and/or air system controller 62. Specifically, sleeves 108 are configured to respond to user inputs including, for example, the target pressure to which each sleeve 108 is to be inflated by air system 20 and/or the desired zone(s) (i.e.: foot zone, calf zone, thigh zone, or some combination thereof) of each sleeve 108 to be inflated by air system 20 if sleeve 108 has multiple zones. The selectable therapy settings further include, for example, the frequency of compression, the duty cycle of the compression cycles, the number of cycles, the time period over which the compression therapy is to take place, or some combination thereof. In some embodiments, the selectable therapy settings include selection of pressure versus time curves (e.g., step up and/or step down curves, ramp up and/or ramp down curves, saw tooth curves, and the like) as well as the parameters for the various types of curves (e.g., pressure setting at each step, duration of each step, duration of ramp up, duration of ramp down, and the like).

Looking to FIGS. 1-4, and as discussed above, compression sleeves 108 are formed to include pneumatic connector 115. Connector 115 is coupled to an outer surface 141 of sleeve 108 and configured to couple conduit 110 thereto. Illustratively, connector 115 extends away from sleeve 108 a distance to reduce the likelihood of long-term contact between conduit 110 and the patient which otherwise results in patient discomfort. In such embodiments, connector 115 may be formed as a pigtail pneumatic connector 115. A pigtail pneumatic connector 115 is formed to couple sleeve 108 and conduit 110 and is extends the length of connector 115 such that conduits 110 are spaced apart from the patient at a greater distance than a non-pigtail pneumatic connector 115. To further avoid patient discomfort resulting from prolonged patient contact with conduits 110, in some embodiments, pneumatic connector 115 includes an outer shell (not shown) formed from a pliable material. In other embodiments, pneumatic connector 115 includes an inner shell (not shown) formed from a rigid material and an outer cover (not shown) encompassing the inner shell and formed from a pliable material.

As shown in FIGS. 1-4, conduit(s) 110 are configured to removeably couple to port 15 and may be embodied as tubes and/or hoses. As such, conduit(s) 110 are configured to extend between port 15 and sleeve(s) 108 and are formed to receive pressurized air from air system 20, 220. Illustratively, at least one port 15 is formed for coupling SCD assembly to air system 20, 220. In some embodiments, multiple ports 15 may be formed for coupling. Ports 15 are formed to configure to tubes 59, 259 and to couple to SCD assembly 14, thereby conveying the stream of pressurized air from air source 58, 258 to SCD assembly 14. In coupling conduit 110 and distribution manifold 60, 260, port 15 configures conduit 110 to guide stream of pressurized air towards sleeve 108. Illustratively, each of a pair of compression sleeves 108 is configured to couple to a respective first end 112 of each of a pair of conduits 110 such that each compression sleeve 108 is configured to provide sequential compression to a lower extremity of the patient. In some embodiments, a multi-port connector (not shown) is provided at second end 113 of conduits 110 to permit simultaneous attachment of multiple conduits 110 to associated coupler(s) (not shown).

Illustratively, main controller 18 is further operable to determine the presence of conduit 110 at port 15. Port 15 is thereby accessible by a caregiver when the patient is positioned on the mattress 22 and configured to couple to multiple SCD assemblies 14. Illustratively, a plurality of SCD assemblies 14 may be removeably coupled to port 15. Further, in embodiments having a plurality of ports 15, each port 15 is configured to couple to SCD assemblies 14 independent of a second port 15. Further, each of the plurality of ports 15, are similarly configured. Additionally, and as discussed above, upon identifying the presence of conduit 110 removeably coupled to port 15, main controller 18 is configured to initiate sequential compression therapy upon identifying the removal of conduit 110 from port 15.

A caregiver may also initiate/terminate therapy by using user interface 70 and inputting the desired action. As such, a particular zone/combination of zone and sleeves 108 may be selected by the caregiver using user interface 70 via user inputs 13. For example, buttons 13 for selection by a user of left and/or right foot sleeves, left and/or right calf sleeves, left and/or right thigh sleeves, or left and/or right combination sleeves such as those described above appear on display screen 76, in some embodiments. It should be appreciated that the compression sleeve 108 on a patient's left leg may be of a different type than that on the patient's right leg. Alternatively or additionally, main controller 18 is operable to determine which type of sleeve 108 is connected to each port 15 based on the time it takes to inflate the particular sleeve 108 to a target pressure as measured by pressure sensors 64. After main controller 18 makes the sleeve type determination for the one or more sleeves 108 coupled to port(s) 15, such information is displayed on GUI 76.

Main controller 18 is illustratively configured to automatically communicate to air system controller 62 to stop therapy in response to a signal from sensors 64 conveying a disconnection of conduits 110 and ports 15. Sensors 64 may be in communication with main controller 18 and are configured to convey data concerning conduit 110. Both the removal/presence of conduit 110 may be determined in a single algorithmic step due to the integral relationship of the presence/absence of conduit 110 at port 15. In some embodiments, sensors 64 are configured to determine the removal of conduit 110 from port 15 and signal to air system controller 62 the removal of conduit 110. Air system controller 62 may then stop the creation/conveyance of pressurized air flow to SCD assembly 14, thereby removing main controller 18 from the method of use for the additional embodiment.

In some embodiments, upon main controller receiving the data from sensors 64 identifying the presence of conduit 110 at port 15, main controller communicates with scale system 23 which detects the presence of SCD assembly 14 and zeros the scale to zero pounds. This avoids discrepancies in patient weight due to the weight of SCD assembly 14 and is done automatically such that the caregiver does not have to remember to zero the patient support apparatus 12 before measuring the weight of the patient positioned on bed 1.

In some embodiments, the removal of pneumatic therapy device 14 and the associated data is communicated to the main controller 18. Such associated data may include, but is not limited to, the location of pneumatic therapy source 14. This data may then be conveyed between main controller 18 to a wall unit (not shown) and further communicated between the wall unit and a nurse station (not shown).

As discussed above, when SCD assembly 14 is coupled to air system 20, 220, air system 20, 220 senses the presence of SCD assembly 14 and begins the transmission of power and/or pressurized air between SCD assembly 14 and air system 20, 220. Illustratively, such transmission of pressurized air is conveyed through a wired connection to SCD assembly 14. Whereas the transmission of power may be completed wirelessly, illustratively. In other embodiments, the transmission of power may be conveyed through a wired connection. In some embodiments, air system 20, 220 continuously generates the pressurized air stream upon coupling to SCD assembly 14, thereby causing SCD assembly 14 to maintain a desired level of pressure within SCD assembly 14. In other embodiments, air system 20, 220 is pre-programmed to generate pressurized air in cycles, waves, and/or any other desired patterns. In still other embodiments, main controller 18 and air system 20, 220 are in communication such that air system 20, 220 is configured to move between a plurality of pre-programmed patterns in response to user input or automatically in response to sensed pressure values of SCD assembly 14 exceeding a predetermined threshold. Main controller 18, sensors 64, and air system 20, 220 are in communication and further configured to identify the removal of the SCD assembly 14 and, illustratively, stop production of the pressurized air stream within the air system 20, 220.

Therefore, upon identification of SCD assembly 14 coupling to air system 20, 220, air system 20, 220 communicates such coupling to main controller 18. Main controller 18 is configured to communicate with user interface 70 such that user interface 70 is updated to control operation of SCD assembly 14 by allowing access to air system 20, 220 via user interface 70. Such access allows for a caregiver to input/receive patient data at a centralized location on patient support apparatus 12. Illustratively, user interface 70 is configured to alert the caregiver upon disconnection of SCD assembly 14 and air system 20, 220 and/or other interruptions to the therapy therein provided.

In further embodiments, conduit 110 is formed as a pneumatic conduit and is made of an elastic, non-porous material configured to expand in length when pressurized with air. Such elastic, non-porous material is configured to move between an extended length (not shown) and a storage length (not shown) in response to the presence of pressurized air therein. Storage length has a distance measuring less than a distance of extended length, and, as such, storage length has a surface area measuring less than a surface area of extended length. At rest, pneumatic conduit has the storage length. Upon actuation of source of pressurized air 58, 258, pneumatic conduit reacts to the presence of pressurized air by increasing the length and surface area of pneumatic conduit. As such, so long as the pressurized air is directed into pneumatic conduit, pneumatic conduit will maintain the extended length. Therefore, a production and direction of the majority of the pressurized air into conduit is to be ceased before conduit returns to storage length. This permits conduit to be stored in a variety of manners due to the decreased length and surface area of conduit.

In other embodiments in which conduit 110 is formed as a pneumatic conduit, pneumatic conduit is configured to include a break away coupler (not shown). Break away coupler may be positioned between sleeve 108 and conduit 110 and/or between a first conduit section extending between sleeve 108 and break away coupler and a second conduit section extending between break away coupler and second end of conduit. Break away coupler is configured to disconnect from conduit 110 when longitudinal forces in line with conduit 110 exceed a pre-determined breaking force of coupler. The force needed to decouple coupler and conduit 110 is substantially greater than the longitudinal force created by the pressurized air within conduit 110 during operation of SCD assembly 14 and/or other therapies. As such, actuation of SCD assembly 14 does not cause coupler to break away from conduit 110 unless such force exceeds the breaking force of coupler. Further, the breaking force is substantially less than the force exerted upon conduit 110 by a leg of the patient when conduit 110 creates a fall risk. Break away coupler, therefore, is configured to break away from conduit 110 in response to the patient tripping over conduit 110, thereby resulting in a cessation of therapy until coupler is reattached to conduit 110. As such, upon main controller 18 ceasing production of pressurized air and the caregiver removal of SCD assembly 14 and SCD assembly 14 is decoupled from port 15.

In other embodiments, main controller 18 is configured to communicate with the scale system 23 to correlate the weight of the patient positioned on patient support apparatus 12 to the amount of pressure that should be generated in sleeves 108 of pneumatic therapy system 14. Main controller 18 is configured to monitor and adjust the pressure within sleeves 108 such that the desired pressure settings are utilized. The weight of the patient may be communicated wired or wirelessly between pneumatic therapy device 14 and main controller 18. The scale system 23 may also be used to determine when a patient exits the bed and alert the caregiver of the violation as well as indicate that the pneumatic therapy device 14 is not in use. Illustratively, this may be accomplished via the algorithm shown in FIG. 7.

Figure 7:
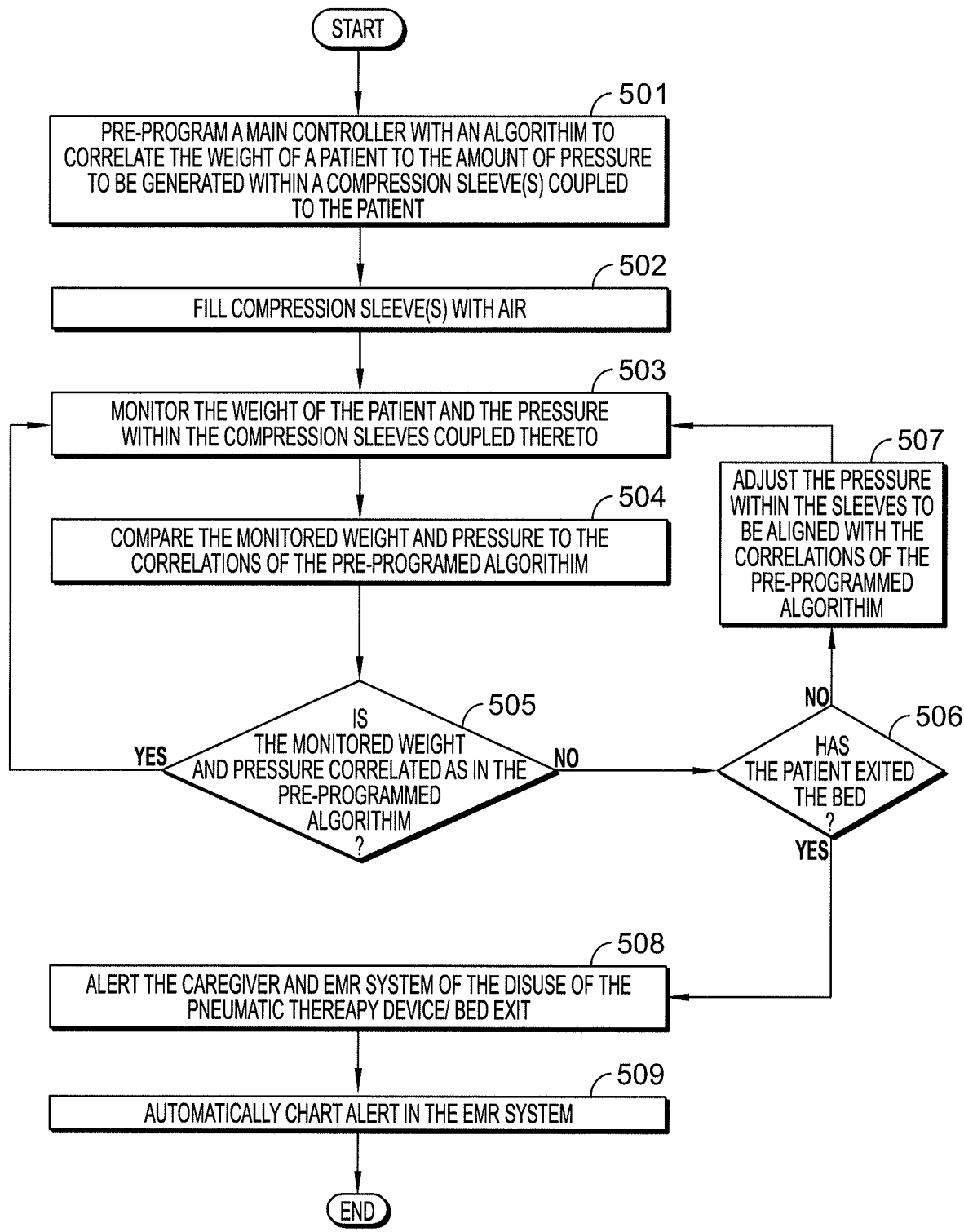
FIG. 7 is a flowchart showing an algorithm pre-programmed in the main controller and configuring the main controller to determine if the patient has left the bed based on the weight of the patient on the bed and the pressure within the pneumatic therapy device.

The algorithm as shown in FIG. 7 includes pre-programming main controller 18 with an algorithm to correlate the weight of the patient on the patient support apparatus 12 to the amount of pressure to be generated within the compression sleeve(s) 108 coupled to the patient as shown in step 501. At step 502, the pressure sleeve(s) 108 are filled with air from an air source 58, 258. The scale system 23 configured to monitor the weight of the patient and the pressure within the sleeve(s) 108 coupled thereto at step 503. At step 504, the monitored weight and pressure is compared to the correlations of the pre-programmed algorithm. Main controller 18 is configured to determine if the monitored weight and pressure are correlated as in the pre-programmed algorithm at step 505. If the monitored weight and pressure are correlated as in the pre-programmed algorithm, then the main controller 18 and scale system 23 return to monitoring the weight of the patient and associated pressure at step 503. If the monitored weight and pressure are not correlated as in the pre-programmed algorithm, then the main controller 18 determines if the patient has exited patient support apparatus 12 at step 506. If the patient has not left patient support apparatus 12, the pressure within sleeve(s) is adjusted to be aligned with the pre-programmed correlations at step 507. After step 507, main controller 18 and sensors 64 return to continue monitoring the weight and associated pressure of the patient at step 503. If it is determined that the patient has left patient support apparatus 12 at step 506, an alert is communicated to the caregiver and EMR system notifying him/her/them of the disuse of the pneumatic therapy device 14/patient support apparatus 12 exit at step 508. At step 509, the information conveyed to the caregiver and EMR system is automatically charted in the EMR system.

In some embodiments, main controller 18 of patient support apparatus 12, pneumatic therapy device 14, and EMR system cooperate to associate patient support apparatus 12 and pneumatic therapy device 14 and communicate the association to EMR system. Further, EMR system is configured to associate a specific therapy with patient support apparatus 12 and pneumatic therapy device 14. Illustratively, this may be accomplished via the algorithm shown in FIG. 8.

Figure 8:
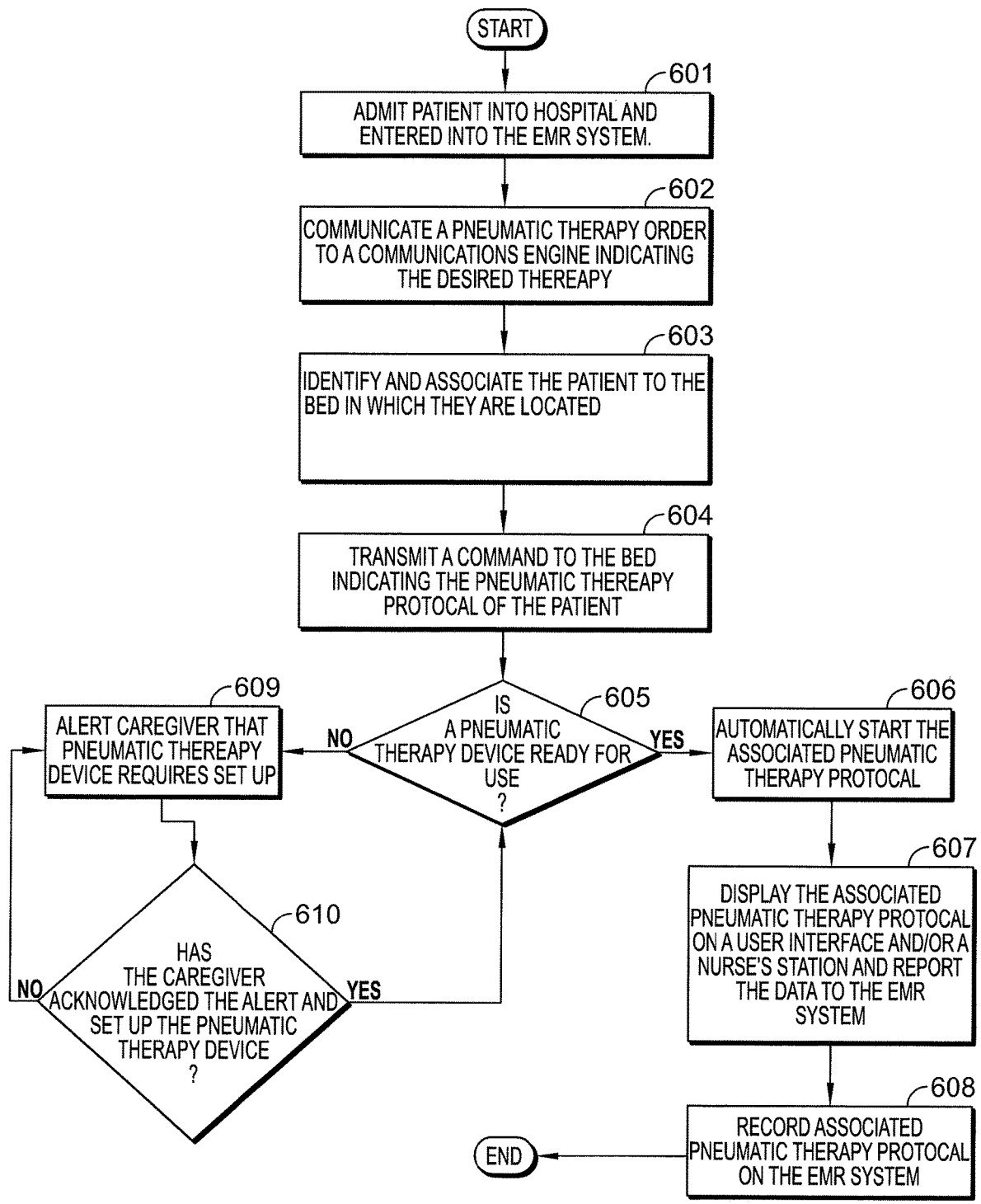
FIG. 8 is a flowchart showing an algorithm pre-programmed in the main controller and configuring the main controller to associate the bed and pneumatic therapy system with the patient positioned on the bed and automatically start a therapy protocol associated with the patient.
Figure 9:
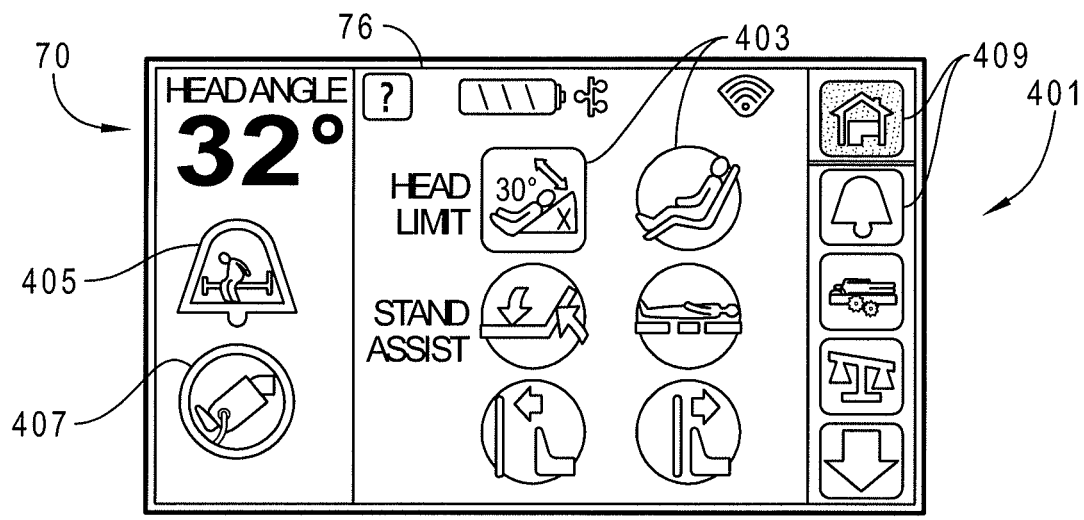
FIG. 9 is a plan view of a graphical user interface (GUI) of FIG. 1 coupled to the bed and showing the home screen of an integrated DVT prevention system screen flow.

The algorithm as shown in FIG. 8 includes admitting the patient into a hospital and entering patient information into EMR system at step 601. At step 602, a pneumatic therapy order is communicated to a communications engine indicating the desired therapy for the patient associated with patient support apparatus 12. The communications engine associates the patient to the patient support apparatus 12 at step 603. At step 604, the communications engine communicates a command to patient support apparatus 12 indicating the desired pneumatic therapy protocol for the patient. Main controller 18 is configured to determine if pneumatic therapy device 14 is ready for use at step 605. If pneumatic therapy device 14 is ready for use, main controller 18 automatically begins the associated pneumatic therapy protocol at step 606. The associated pneumatic therapy protocol is displayed on user interface 70 and/or nurse's station 176 and reported to EMR system at step 607. At step 608, the associated pneumatic therapy protocol is recorded on EMR system. Returning to step 605, if it is determined that pneumatic therapy device 14 is not ready for use, then main controller 18 communicates an alert to the caregiver that pneumatic therapy device 14 requires set up at step 609. At step 610 main controller determines if the caregiver has acknowledged the alert and set up the pneumatic therapy device 14. If not, main controller 18 returns to step 609 and continues to communicate the alert to the caregiver that pneumatic therapy device 14 requires set up. If the caregiver has acknowledged the alarm, then main controller 18 returns to step 605 to determine if pneumatic therapy device 14 is ready for use. In some embodiments, the communications engine is further configured to communicate the patient data to the associated patient support apparatus 12 such that the patient data may be accessed therefrom.

In other embodiments, user interface 70 of patient support apparatus 12 is configured automatically detect the coupling of sleeve(s) 108 to patient support apparatus 12 using a sleeve(s) 108 formed as a smart sleeve(s) 108, temperature sensor(s) 89 coupled to sleeve(s) 108, and/or user interface 70. Temperature sensor 89 is configured to measure the temperature of the patient and provides feedback that sleeve(s) are coupled to the patient. In some embodiments, smart sleeve(s) 108 is configured to sense moisture, patient heartbeat, and/or air bladder shape to ascertain if sleeve(s) 108 is coupled to the patient. Smart sleeve(s) 108 may also be coupled to patient support apparatus 12 using s smart connector (not shown) configured to provide feedback to patient support apparatus 12 that sleeve(s) 108 are coupled to patient support apparatus 12 and automatically initiate pneumatic therapy. In sensing the coupling of sleeve(s) 108 to the patient, main controller 18 may also consider the air volume changes within conduit(s) 110. In some embodiments, an electrical switch connection is maintained once sleeve(s) 108 are coupled to patient support apparatus 12.

User interface 70 is configured to communicate with patient support apparatus 12 and sleeve(s) 108 to display the coupling via an indication, such as user interface 70 turning green to notify proper coupling and red to notify improper coupling. Compliance to pneumatic therapy may also be tracked and automatically logged in the EMR system using the NAVICARE SMARTSYNC® application.

Figure 10:
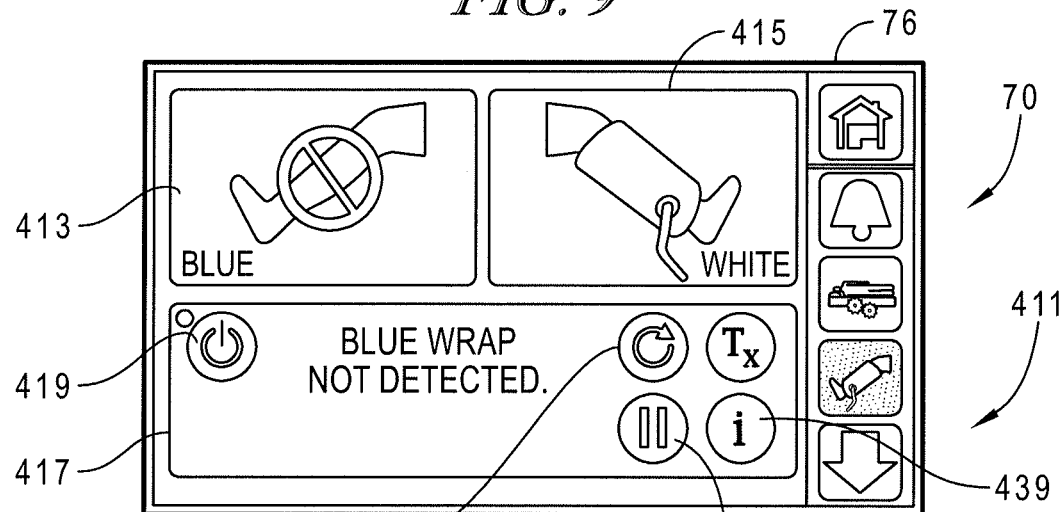
FIG. 10 is a plan view of the GUI of FIG. 9 showing a screen indicating that one of the compression sleeves is not coupled to the bed.

In some embodiments, as shown in FIGS. 9-21, patient support apparatus 12, pneumatic therapy device 14, and user interface 70 communicate to display the status of the pneumatic therapy device 14 at patient support apparatus 12. Illustratively, such information is displayed on screen 76 of user interface 70. As shown in FIGS. 9-21, user interface 70 is configured to display a home screen 401 having a plurality of bed angle indicators 403, a bed exit alarm 405, a pneumatic therapy alarm 407, and a plurality of other buttons 409 configured to adjust patient support apparatus 12 and/or pneumatic therapy device 14. Upon pressing pneumatic therapy alarm 407 on screen 76, a pneumatic information screen 411 as shown in FIG. 10 may be displayed to communicate that a compression sleeve 108 is not detected. In FIG. 10, compression sleeve 413 is not coupled to patient support apparatus 12 and is displayed in blue to indicate that status. The compression sleeve 415 is coupled to patient support apparatus 12 and displayed in white to indicate the connection. It should be appreciated that other sleeve 108 combinations can be displayed such as white compression sleeve 415 not coupled to the patient support apparatus 12 and blue compression sleeve 413 coupled thereto. Further, screen 76 displays a warning 417 to the caregiver communicating when one of sleeves 108 is uncoupled from patient support apparatus 12.

Figure 11:
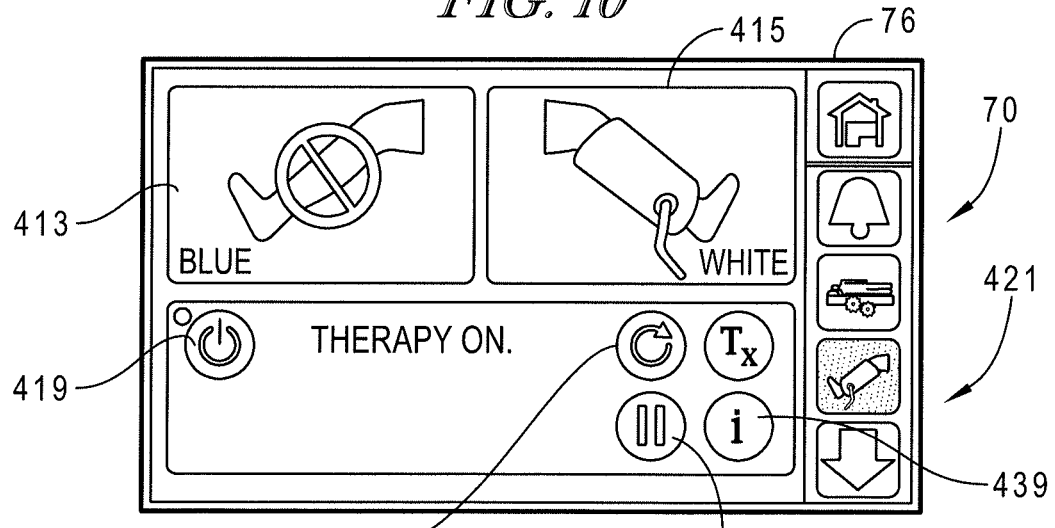
FIG. 11 is a plan view of the GUI of FIG. 9 showing a screen indicating that therapy is on and one compression sleeve is coupled to the bed and receiving compressed air.
Figure 12:
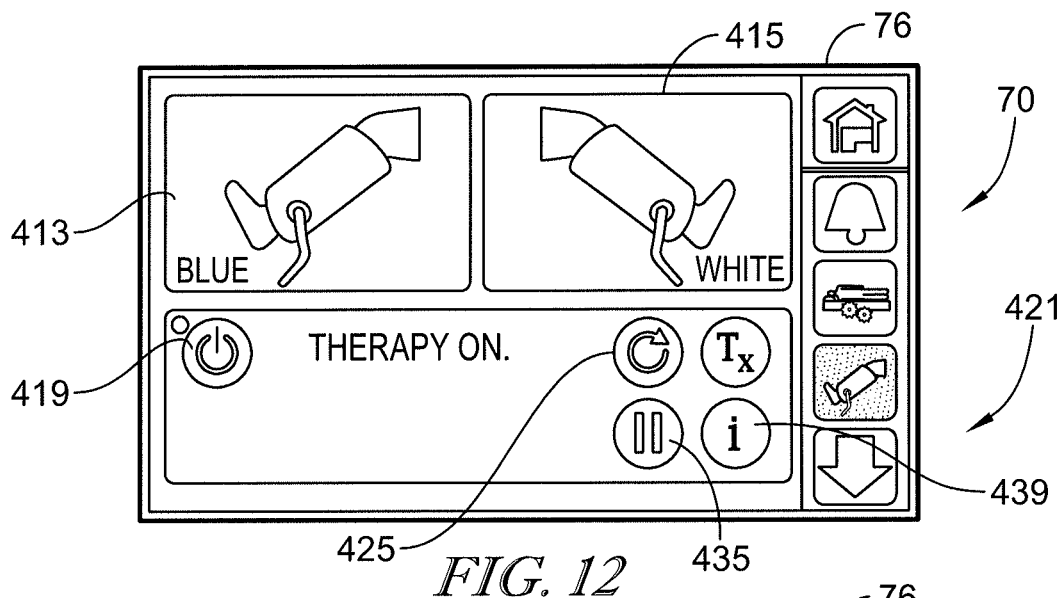
FIG. 12 is a plan view of the GUI of FIG. 9 showing a screen indicating that therapy is on and two compression sleeves are coupled to the bed and receiving compressed air.
Figure 13:
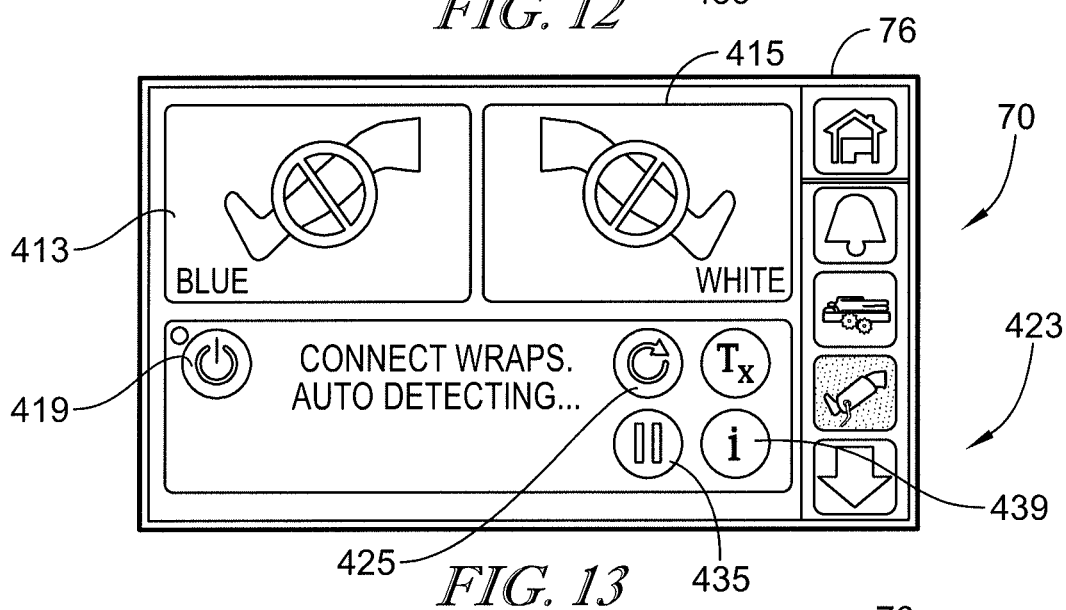
FIG. 13 is a plan view of the GUI of FIG. 9 showing a screen indicating that the main controller is determining if any compression sleeves are coupled to the bed.
Figure 14:
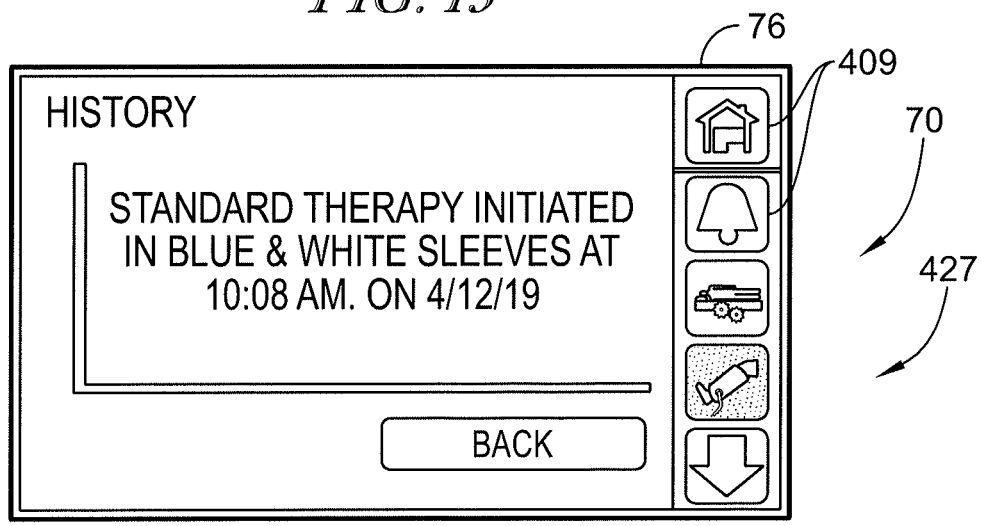
FIG. 14 is a plan view of the GUI of FIG. 9 showing a screen with the patient's therapy history displayed thereon.
Figure 15:
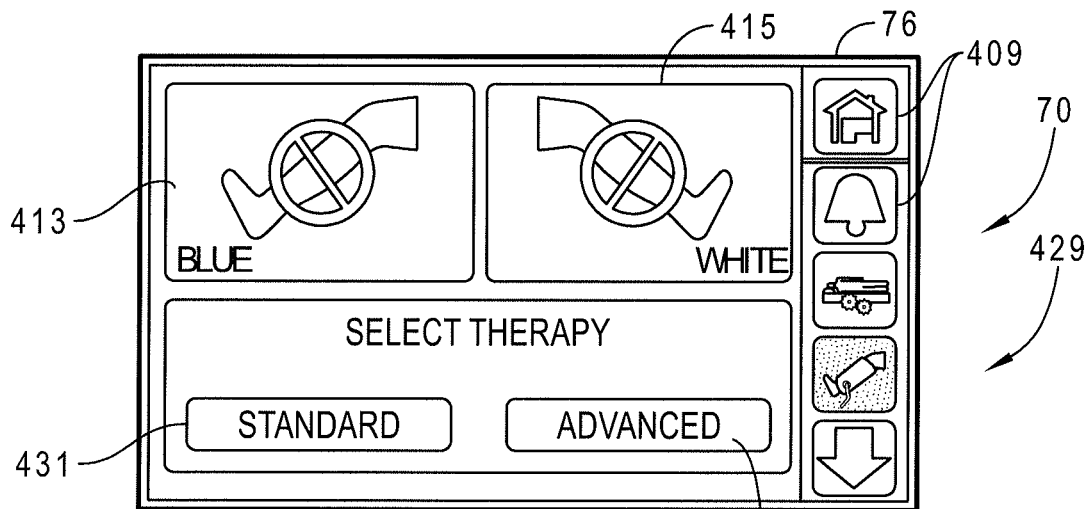
FIG. 15 is a plan view of the GUI of FIG. 9 showing a screen compelling the user to select the type of therapy desired.

Upon therapy initiation by actuation of a power button 419 by the caregiver, screen 76 is further configured to display, as shown in FIG. 11, a current status display 421 communicating information about the current therapy and sleeves 108. In some cases, both compression sleeves 108 are in use during therapy, as shown in FIG. 12. When initially connecting compression sleeves/wraps 108, screen 76 may communicate such actions as shown in FIG. 13 using a status screen 423. Additional buttons on screen 76 may include a history button 425 which when pressed displays a history screen 427 of associated pneumatic therapy device 14 as shown in FIG. 14. Further, if no pre-programmed therapy is associated with patient support apparatus 12 and/or pneumatic therapy device 12, then screen 76 may provide a selection screen 429 having a selection for standard therapy 431 and a selection for advanced therapy 433 as shown in FIG. 15.

Figure 16:
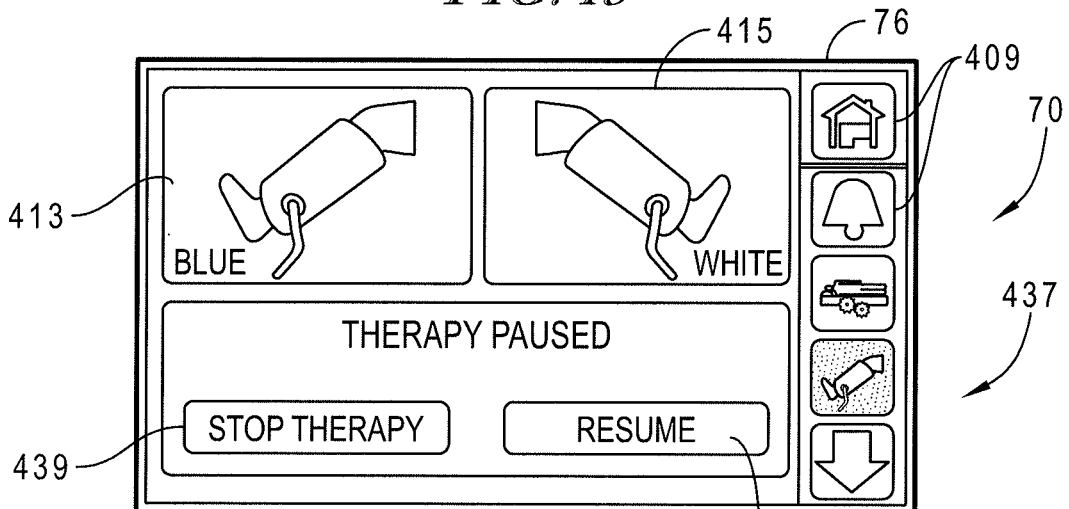
FIG. 16 is a plan view of the GUI of FIG. 9 showing a screen indicating that the therapy is paused.
Figure 17:
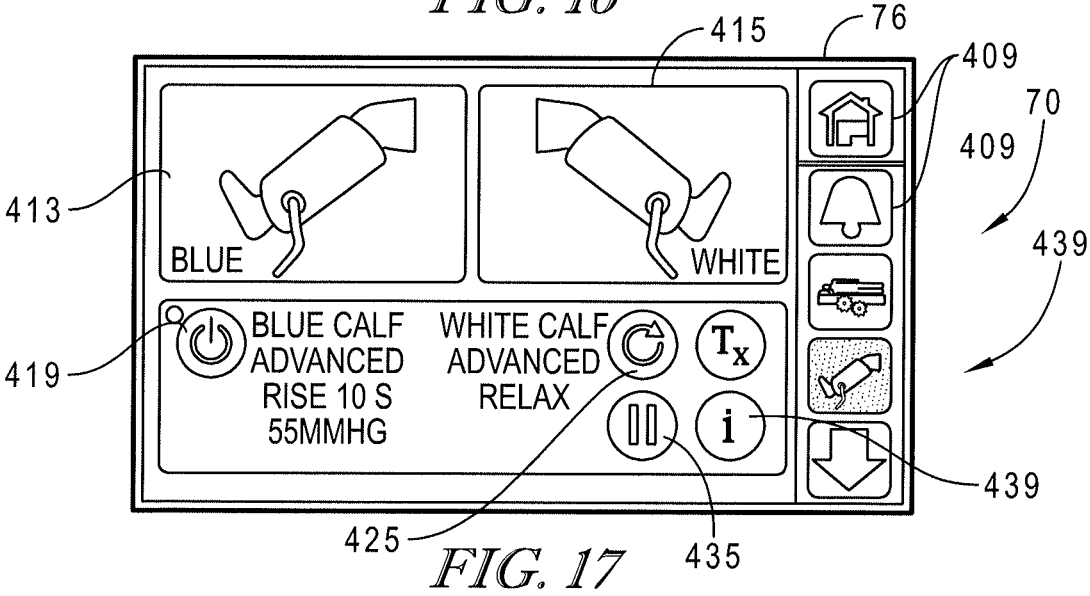
FIG. 17 is a plan view of the GUI of FIG. 9 showing a screen displaying the unique therapy of each compression sleeve.

A pause button 435 may also be included on screen 76 as shown in FIGS. 10-13, and, once selected, is configured to pause therapy provided by pneumatic therapy device 14 and display a pause screen 437 as shown in FIG. 16. Pause screen 437 illustratively displays a stop therapy button 443 configured to terminate the pre-programmed pneumatic therapy and a resume button 441 configured to return to the pre-programmed pneumatic therapy to continue the therapy. An information button 440 may also be included on screen 76 and is configured to display the information associated with each of the sleeve(s) 108 on a data screen 442 as shown in FIG. 17.

Figure 18:
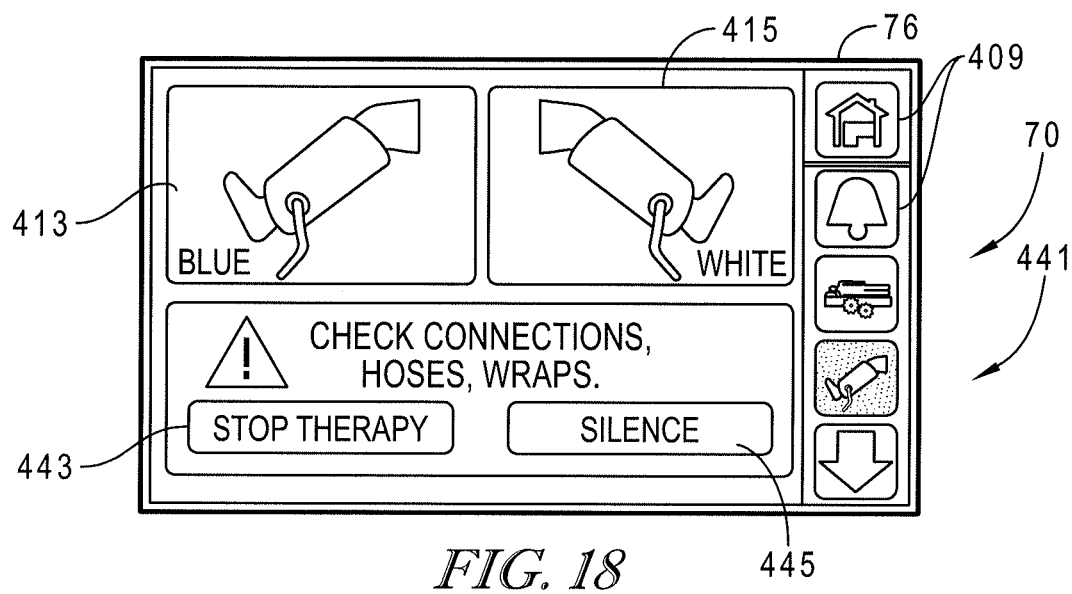
FIG. 18 is a plan view of the GUI of FIG. 9 showing a screen displaying a warning to the caregiver to check the ports, conduits, compression sleeves, and the connections therebetween.

User interface 70 may also be configured to display alerts to the caregiver, as shown in FIGS. 18-21. As shown in FIG. 18, a first alert screen 441 regarding incorrect coupling of each compression sleeve 108 to associated port 15 may be communicated to the caregiver through the user interface 70. Incorrect coupling alert screen 441 includes a stop therapy button 443 configured to stop pneumatic therapy upon actuation thereof and a silence button 445 configured to silence the alert and continue the pneumatic therapy.

Figure 19:
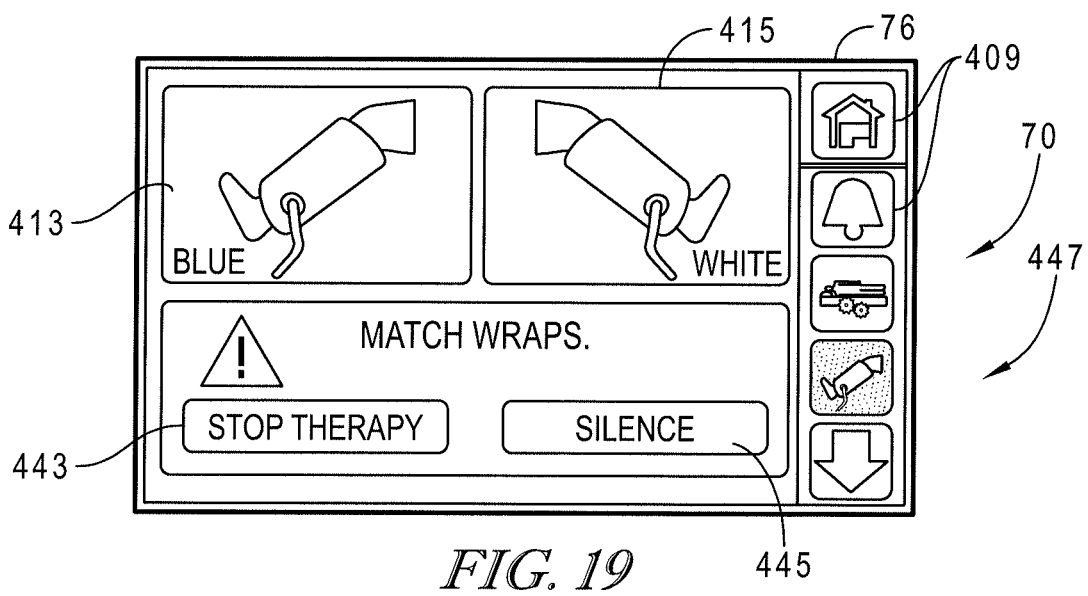
FIG. 19 is a plan view of the GUI of FIG. 9 showing a screen displaying a warning to the caregiver to match the compression sleeves to the matching port.
Figure 20:
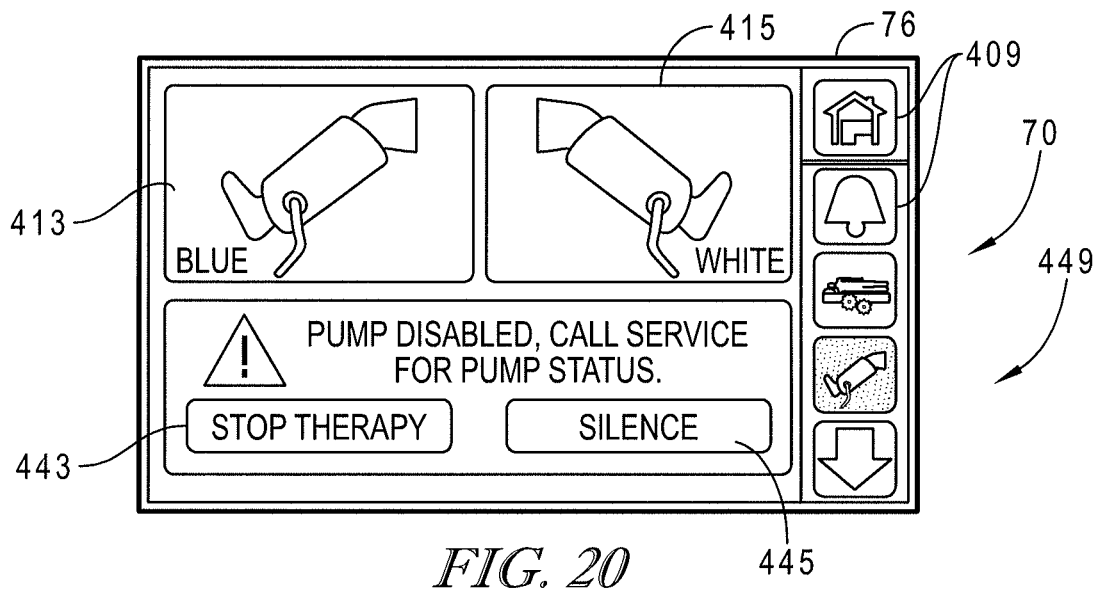
FIG. 20 is a plan view of the GUI of FIG. 9 showing a screen displaying a warning to the caregiver to match the compression sleeves to the associated port.
Figure 21:
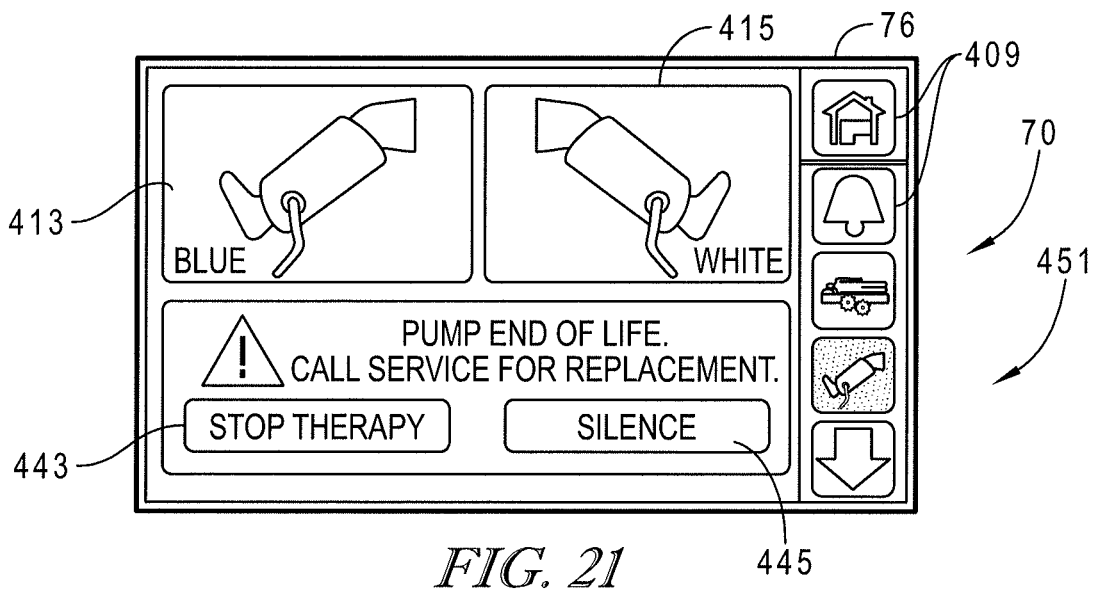
FIG. 21 is a plan view of the GUI of FIG. 9 showing a screen displaying a warning to the caregiver that the source of air is about to die and a replacement should be ordered.

A second alert screen 447 may be displayed on screen 76 and communicate to the caregiver when sleeves 108 do not match as shown in FIG. 19. Similar to FIG. 18, air source disabled alert screen 447 includes a stop therapy button 443 configured to stop pneumatic therapy upon actuation thereof and a silence button 445 configured to silence the alert and continue the pneumatic therapy. A third alert screen 449 may be displayed on screen 76 and communicate to the caregiver when air source 58, 258, 358 is disabled and service should be called for the status of air source 58, 258, 358. Similar to FIGS. 18-19, FIG. 20 shows a third alert screen 449 having a stop therapy button 443 configured to stop pneumatic therapy upon actuation thereof and a silence button 445 configured to silence the alert and continue the pneumatic therapy. A fourth alert screen 451 may be displayed on screen 76 and communicate to the caregiver when air source 58, 258, 358 is at the end of its life and service should be called for a replacement, as shown in FIG. 21. Similar to FIGS. 18-20, FIG. 21 shows a fourth alert screen 451 having a stop therapy button 443 configured to stop pneumatic therapy upon actuation thereof and a silence button 445 configured to silence the alert and continue the pneumatic therapy.

Figure 27:
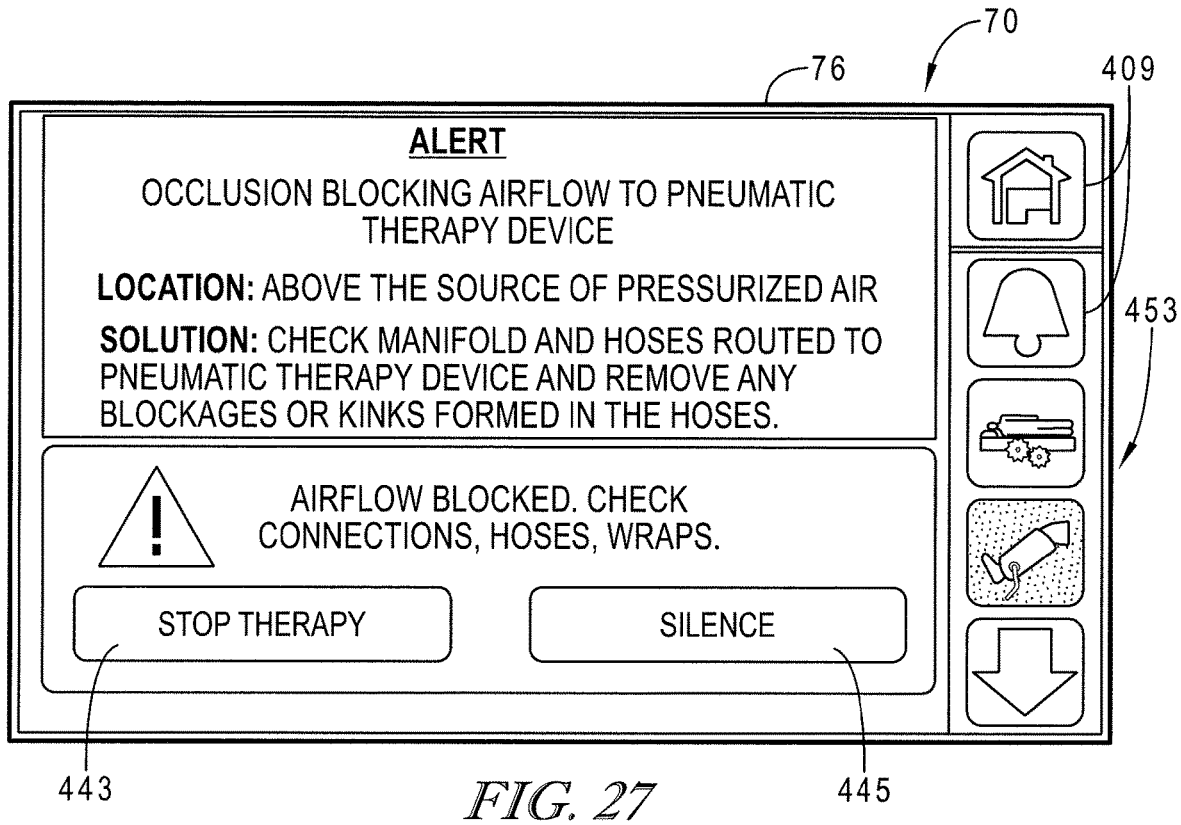
FIG. 27 is a plan view of the GUI of FIG. 9 displaying an alert to the caregiver of an occlusion blocking the airflow to the pneumatic therapy device, the location of the occlusion, and the solution.
Figure 28:
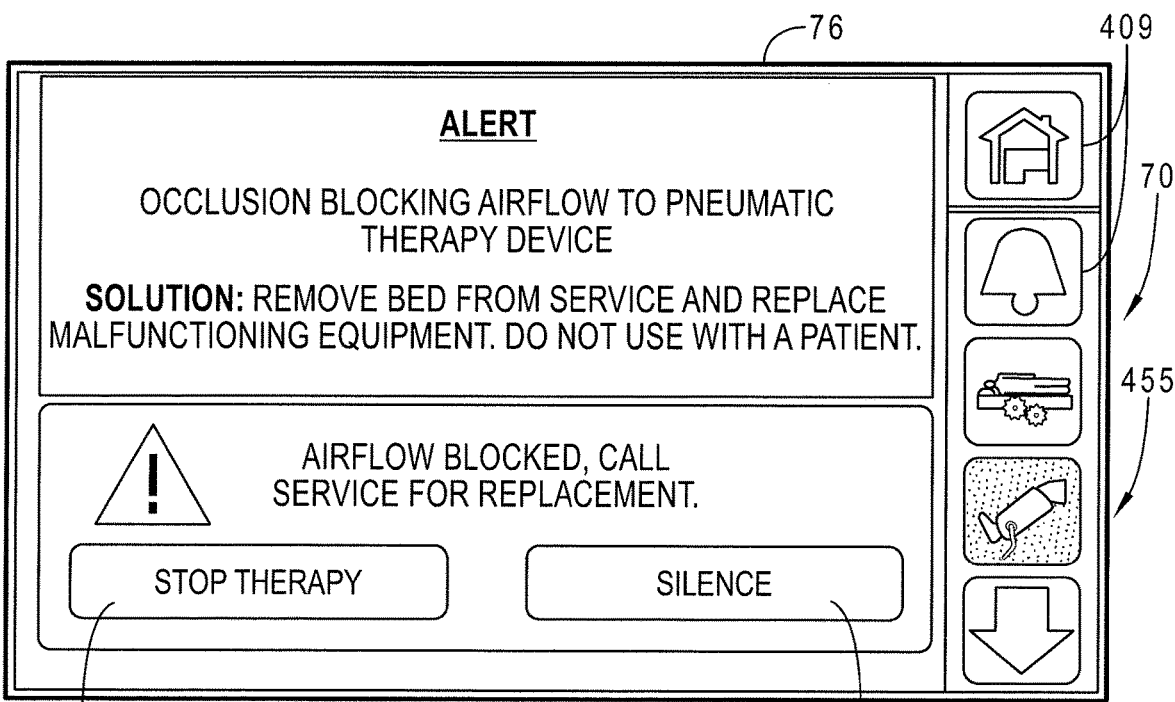
FIG. 28 is a plan view of the GUI of FIG. 9 displaying an alert to the caregiver of an occlusion blocking the airflow to the pneumatic therapy device and the solution.

A fifth alert screen 453 may be displayed on screen 76 and communicate to the caregiver that the airflow is blocked and provides additional information concerning the location of the blockage and the best solution as shown in FIG. 27. Similar to FIGS. 18-21, FIG. 27 shows a fifth alert screen 453 having a stop therapy button 443 configured to stop pneumatic therapy upon actuation thereof and a silence button 445 configured to silence the alert and continue the pneumatic therapy. A sixth alert screen 455 may be displayed on screen 76 and communicate to the caregiver that the airflow is blocked and provides a solution as shown in FIG. 28. Similar to FIGS. 18-21 and 27, FIG. 28 shows a sixth alert screen 455 having a stop therapy button 443 configured to stop pneumatic therapy upon actuation thereof and a silence button 445 configured to silence the alert and continue the pneumatic therapy.

Figure 22:
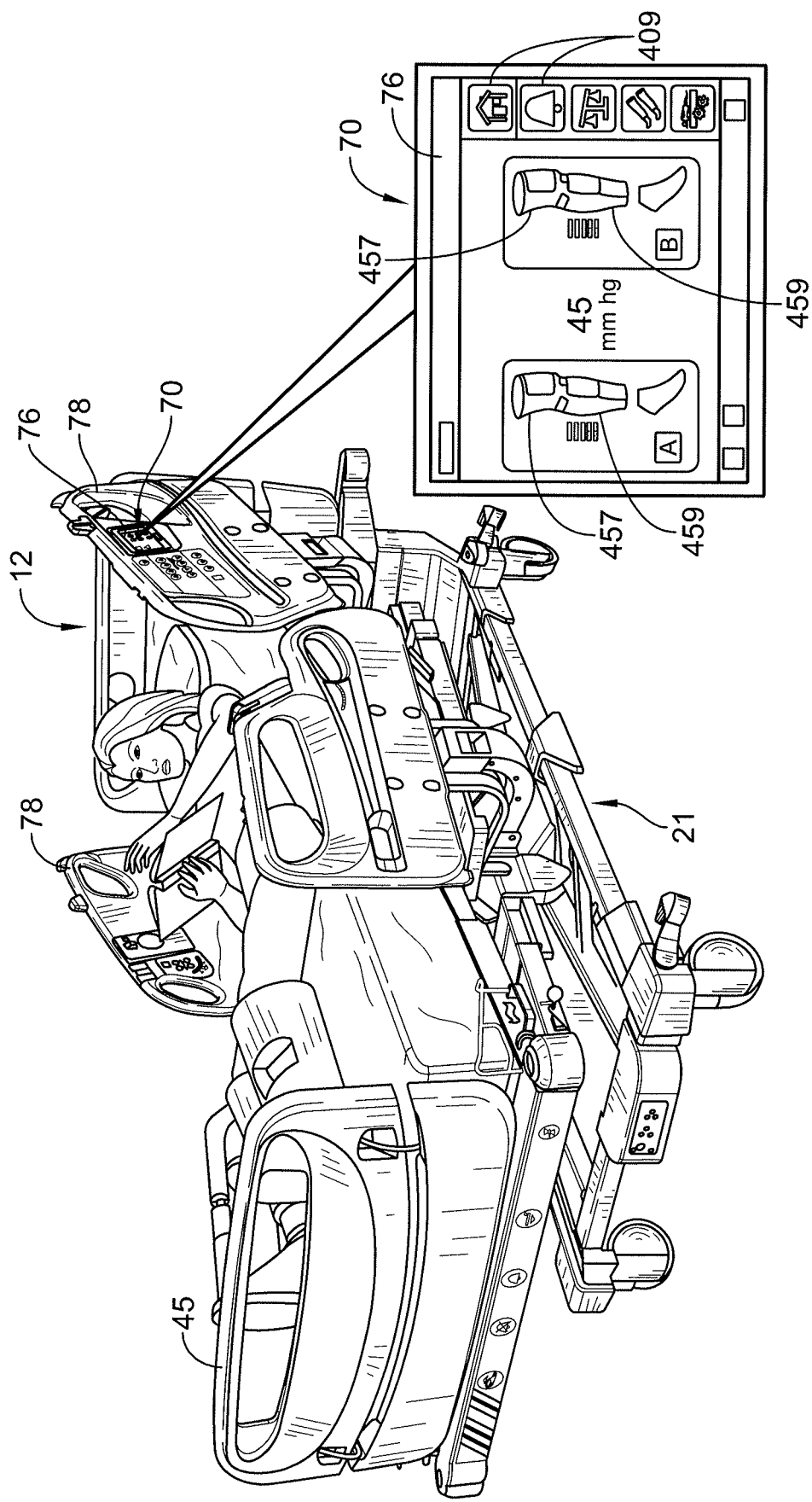
FIG. 22 is perspective view of the bed of FIGS. 1-4 showing the GUI and location at which the screens shown in FIGS. 9-21 may be viewed.

In other embodiments, as shown in FIG. 22, user interface 70 is configured to display additional information about pneumatic compression device 14 and permit selection of a specific sleeve 108 and area thereon in which to initiate therapy. Illustratively, user interface 70 shows each sleeve 108 having multiple sections such as a thigh section (not shown), a knee section 457 and a calf section 459 configured to operate independent of the other. User interface 70 displays information regarding pneumatic therapy device 14 coupled to patient support apparatus 12 and permits selection and initiation of therapy at patient support apparatus 12 using user interface 70.

Figure 23:
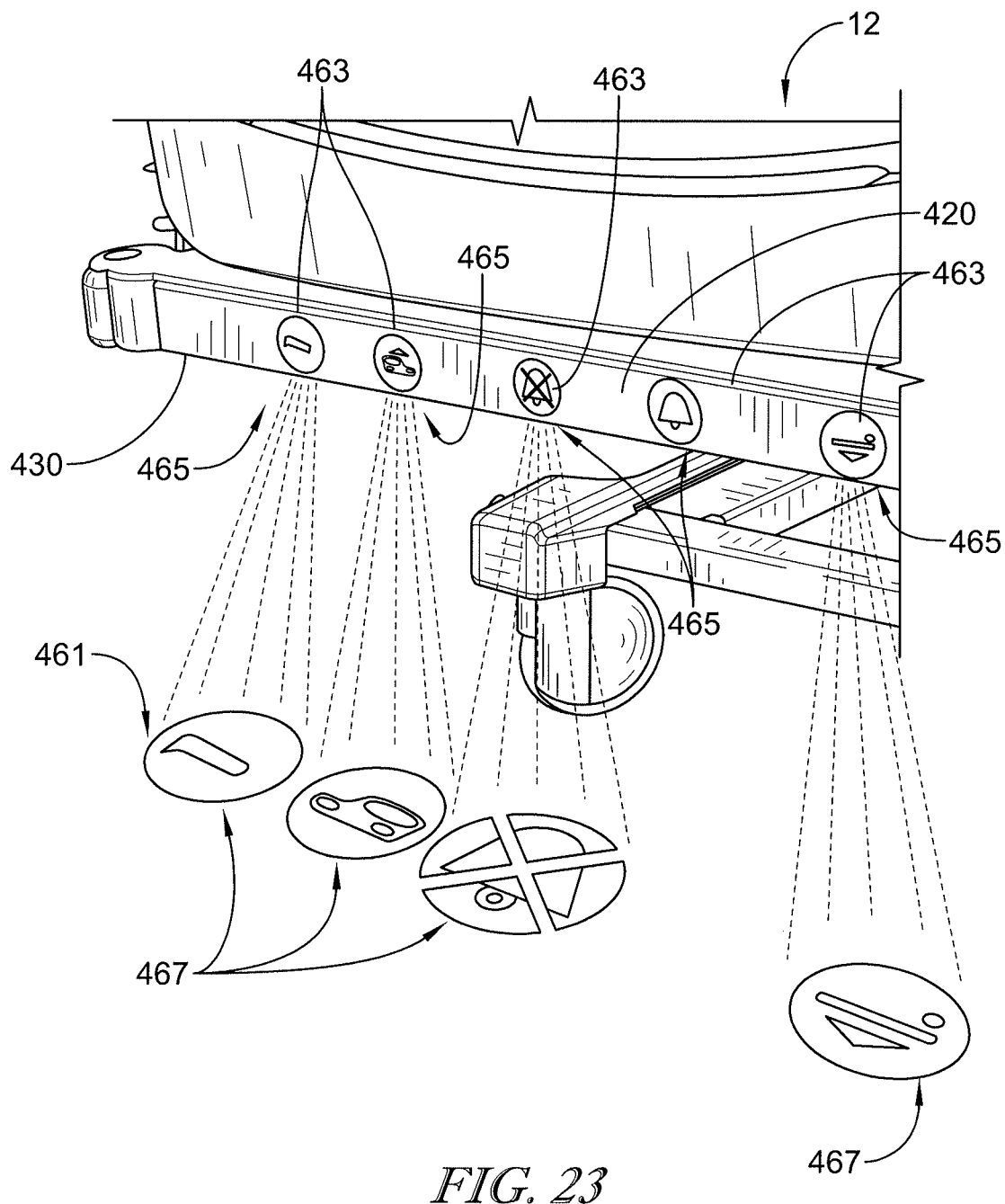
FIG. 23 is a perspective view of the foot end of an embodiment of the bed of FIG. 1 showing an indicator of the status of the pneumatic therapy system projected onto the floor of the patient's room.

In other embodiments, patient support apparatus 12 is formed to include a foot rail 83 extending perpendicular to axis 40 and including a plurality of foot end indicators 463 and a plurality of foot end projectors 465 as shown in FIG. 23. Foot end projectors 465 are configured to display a plurality of symbols 467 using a SAFEVIEW® system of patient support apparatus 12 upon a floor 461 of the patient's room. Illustratively, such symbols 467 are controlled via user interface 70 of patient support apparatus 12 and may show any combination of a plurality of patient support apparatus 12 alerts, the angle of patient support apparatus 12, SCD assembly 14 status, incontinence detection, siderail 78, 80 position, and/or other information pertinent to the care of the patient positioned in patient support apparatus 12. Foot end indicators 463 are formed in an outer surface 420 of foot rail 83 and configured to be viewed by a caregiver from a distance. Illustratively, the caregiver is able to see symbols 467 from a hallway passing by a door into the patient's room. Foot end projector 465 is formed to show the same symbols 467 as foot end indicator 463 and is coupled to a bottom surface 430 of foot rail 83. Projector 465 is configured to project an active and/or static symbol 467 onto the floor of the patient's room. Such active symbols are configured to change between a plethora of pre-programmed symbols 467. Illustratively, symbols 467 shown in green indicate a good status. Whereas symbols 467 shown in flashing yellow indicate an issue/to check user interface 70 and those shown in white indicate that pneumatic therapy device 14 is available for use/on standby.

Figure 24:
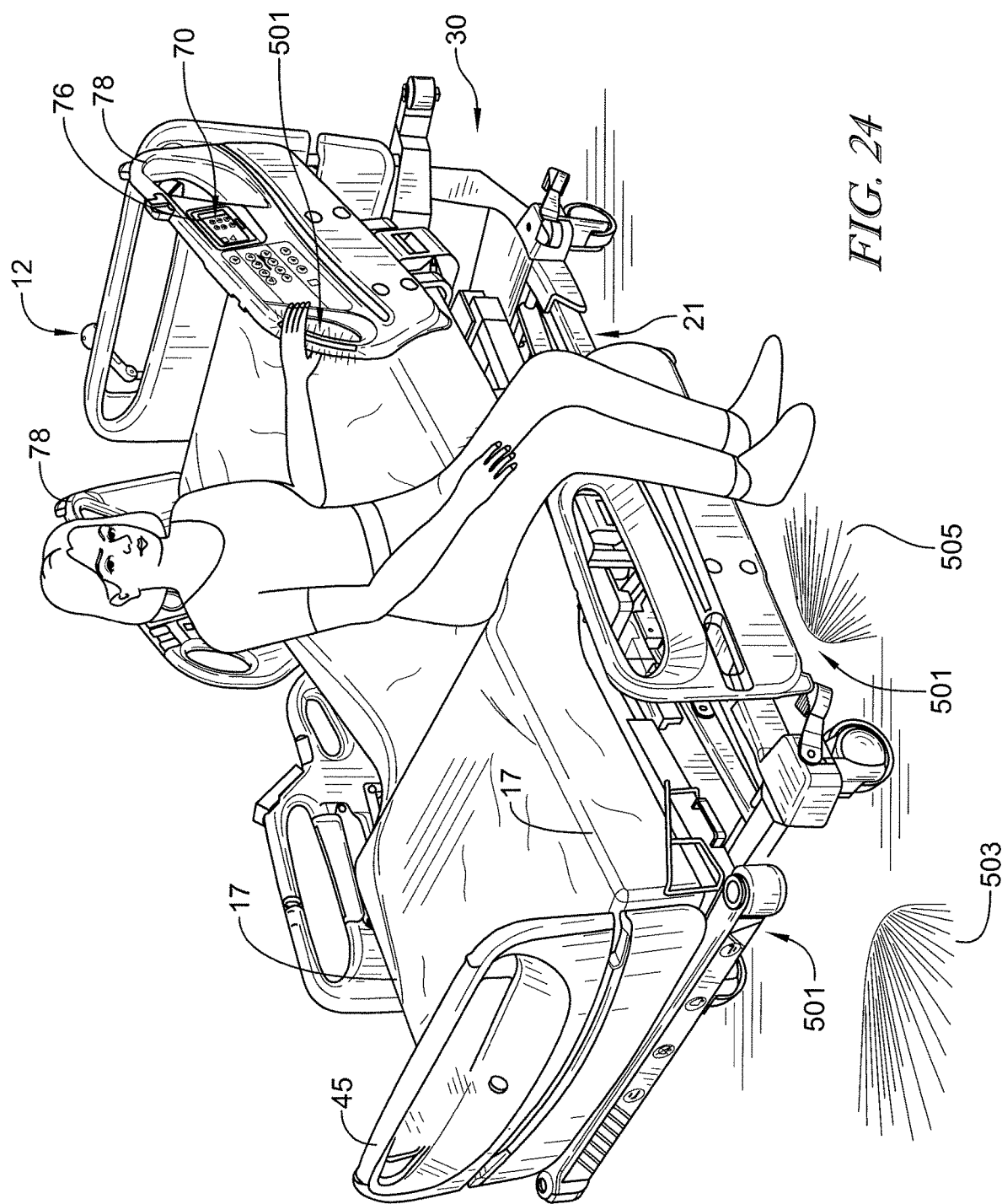
FIG. 24 is a perspective view of the bed of FIGS. 1-4 showing nightlights coupled to the frame of the bed and the siderails.
Figure 26:
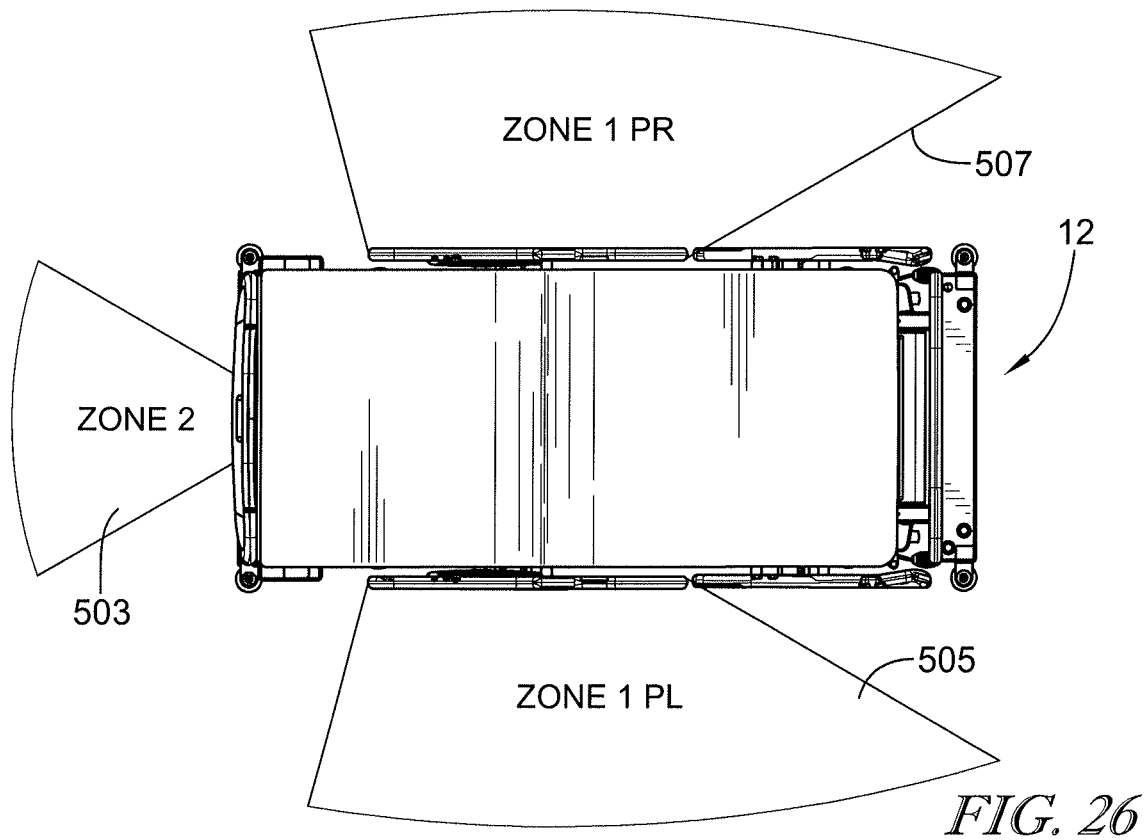
FIG. 26 is a diagrammatic top plan view showing the bed of FIG. 24 showing the range of luminance from the nightlights.

In some embodiments, patient support apparatus 12 is formed to include a plurality of nightlights 501 coupled below upper frame assembly 30 and configured to provide light in a particular zone, as shown in FIGS. 24 and 26. Illustratively, three separate LED assemblies 501 are positioned at foot end 26 of patient support apparatus 12 and configured to illuminate a second zone 503, three separate LED assemblies 501 are positioned at a at a first side 17 of patient support apparatus 12 and configured to illuminate a first right zone 505, and three separate LED assemblies 501 are positioned at a second side 17 opposite first side and configured to illuminate a first left zone 507. An additional nightlight 501 may be coupled to siderail 78 and configured to illuminate the associated siderail 78 area. Each nightlight 501 is configured to operate independently of the other. In some embodiments, nightlights 501 are positioned at the sides 17 of patient support apparatus 12 to illuminate in conjunction with patient movement towards the side 17 of patient support apparatus 12 as measured by pressure sensors 64 coupled to patient support apparatus 12. Further, foot end nightlights 501 are configured to automatically illuminate upon pressure sensors 64 identifying patient movement and further configured to remain on for about 15 minutes after sensing such movement.

Figure 25:
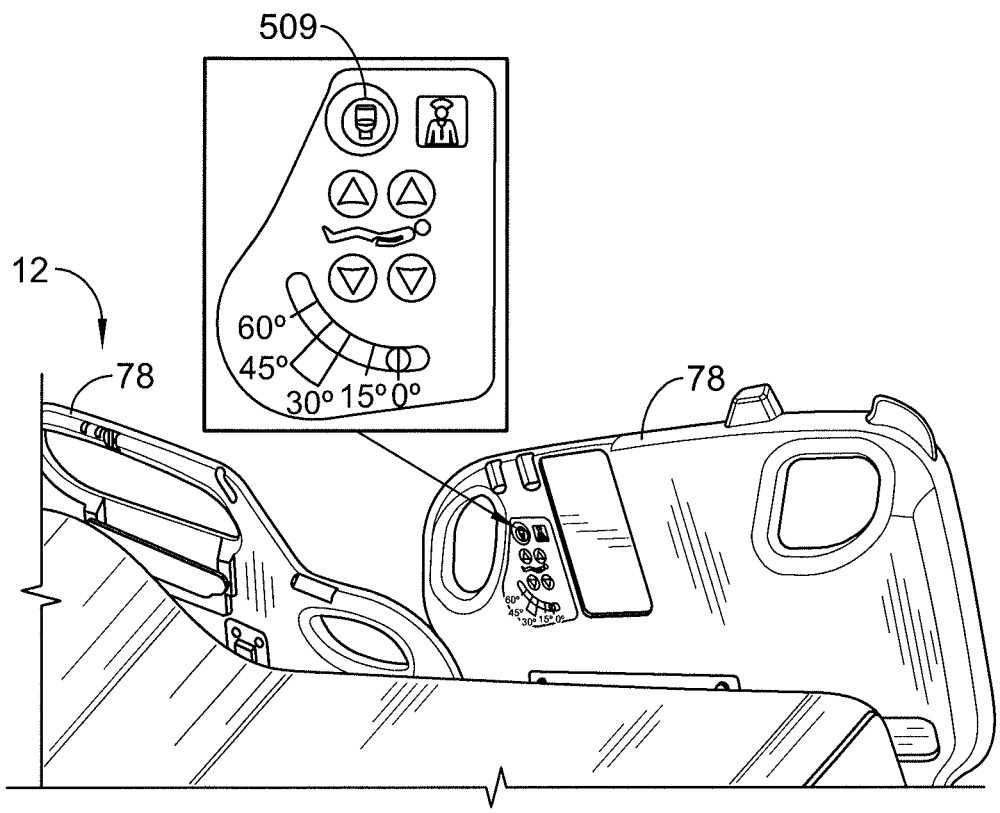
FIG. 25 is an elevation view of the siderail of the bed of FIGS. 1-4 showing the inputs configured to adjust the pneumatic therapy.

In some embodiments, a nightlight button 509 may be formed in siderail 78 and configured to initiate illumination of any combination of second zone 703, first right zone 705 and first left zone 707, as shown in FIG. 25. The patient/caregiver may choose to initiate nightlights 701 when the patient needs to use the restroom or otherwise temporarily exit patient support apparatus 12. Further, such nightlights 701 may be configured to automatically turn off after a pre-determined amount of time. In other embodiments, the nightlights 701 are configured to turn off in response to the patient re-selecting nightlight button 709. In still other embodiments, the patient may wear a BLUETOOTH®, near field, RFID, and/or another trackable device sensed by patient support apparatus 12 which would automatically turn off nightlights 701 upon identifying that the patient has re-entered patient support apparatus 12.

Although certain illustrative embodiments have been described in detail above, variations and modifications exist within the scope and spirit of this disclosure as described and as defined in the following claims.

The invention claimed is:

1. A therapy system comprising
a pneumatic therapy device a including a compression sleeve and a conduit having a first end coupled to the compressions sleeve and a second end,
a patient support apparatus, the patient support apparatus including a frame including a scale system, a source of pressurized air, a distribution assembly including a conduit for directing a flow of pressurized air from the source of pressurized air, an outlet coupleable to the second end of the conduit of the pneumatic therapy device, and a sensor for detecting a pressure, and a controller including a processor and a memory device, the memory device including instructions that are executable by the processor to control the source of pressurized air, distribution system, and user interface, the instructions cause the controller to be operable to determine the weight of a patient on the frame with the scale system, correlate the weight of the patient with an amount of pressure to be applied to the patient by the pneumatic therapy device, and operate the source of pressurized air and distribution assembly to operate the pneumatic therapy device at a correlated pressure, wherein the memory device includes further instructions that, when executed by the processor, cause the controller to determine if the pressure in the sleeve of the pneumatic therapy device meets a pre-programmed correlation with the weight sensed by the scale system, and, if it does, continue to operate the pneumatic therapy device based on the pre-programmed correlation.

2. The therapy system of claim 1, wherein the memory device includes further instructions that, when executed by the processor, cause the controller to monitor the pressure in the sleeve of the pneumatic therapy device and the weight of the patient and use the pressure and weight together as inputs into a control algorithm for controlling the operation of the pneumatic therapy device.

3. The therapy system of claim 2, wherein the memory device includes further instructions that, when executed by the processor, cause the controller to determine if the pressure in the sleeve of the pneumatic therapy device meets the pre-programmed correlation with the weight sensed by the scale system, and, if it does not, determine whether the patient has exited the bed.

4. The therapy system of claim 3, wherein the memory device includes further instructions that, when executed by the processor, cause the controller, in response to determining that the patient has not exited the bed, adjust the pressure within the sleeve to match with the pre-programmed correlation to the weight of the patient.

5. The therapy system of claim 3, wherein the memory device includes further instructions that, when executed by the processor, cause the controller, in response to determining that the patient has exited the bed, provide an alert to a caregiver that the pneumatic therapy device is not being used properly and automatically chart the condition in an electronic medical records system.

6. The therapy system of claim 3, wherein the memory device includes further instructions that, when executed by the processor, cause the controller, in response to determining that the patient has exited the bed, to automatically chart the condition in an electronic medical records system.

7. The therapy system of claim 1, wherein the memory device includes further instructions that, when executed by the processor, cause the controller, in response to determining that the patient has not exited the bed, adjust the pressure within the sleeve to match with the pre-programmed correlation to the weight of the patient.

8. The therapy system of claim 1, wherein the memory device includes further instructions that, when executed by the processor, cause the controller, in response to determining that the patient has exited the bed, provide an alert to a caregiver that the pneumatic therapy device is not being used properly and automatically chart the condition in an electronic medical records system.

9. The therapy system of claim 1, wherein the memory device includes further instructions that, when executed by the processor, cause the controller, in response to determining that the patient has exited the bed, to automatically chart the condition in an electronic medical records system.

10. The therapy system of claim 1, wherein the memory device includes further instructions that, when executed by the processor, cause the controller, in response to determining that the patient has exited the bed, provide an alert to a caregiver that the pneumatic therapy device is not being used properly.

11. The therapy system of claim 2, wherein the memory device includes further instructions that, when executed by the processor, cause the controller, in response to determining that the patient has exited the bed, provide an alert to a caregiver that the pneumatic therapy device is not being used properly.

12. The therapy system of claim 7, wherein the memory device includes further instructions that, when executed by the processor, cause the controller, in response to determining that the patient has exited the bed, provide an alert to a caregiver that the pneumatic therapy device is not being used properly.

13. The therapy system of claim 1, wherein the memory device includes further instructions that, when executed by the processor, cause the controller to alert a caregiver when the pressure of the pneumatic therapy device exceeds a pre-programmed threshold for the particular patient.

14. The therapy system of claim 2, wherein the memory device includes further instructions that, when executed by the processor, cause the controller to alert a caregiver when the pressure of the pneumatic therapy device exceeds a pre-programmed threshold for the particular patient.

15. The therapy system of claim 7, wherein the memory device includes further instructions that, when executed by the processor, cause the controller to alert a caregiver when the pressure of the pneumatic therapy device exceeds a pre-programmed threshold for the particular patient.

16. A method of operating a therapy system that includes a pneumatic therapy device a including a compression sleeve, a patient support apparatus, the patient support apparatus including a frame including a scale system, a source of pressurized air, and an air distribution assembly, the method comprising the steps of:

determining the weight of a patient on the frame with the scale system, correlating the weight of the patient with an amount of pressure to be applied to the patient by the pneumatic therapy device, operating the source of pressurized air and distribution assembly to operate the pneumatic therapy device at a correlated pressure, and determining if the pressure in the sleeve of the pneumatic therapy device meets a pre-programmed correlation with the weight sensed by the scale system, and, if it does, continuing to operate the pneumatic therapy device based on the pre-programmed correlation.

17. The method of claim 16, further comprising the step of:

monitoring the pressure in the sleeve of the pneumatic therapy device and the weight of the patient and use the pressure and weight together as inputs into a control algorithm for controlling the operation of the pneumatic therapy device.

18. The method of claim 16, further comprising the steps of:

determining if the pressure in the sleeve of the pneumatic therapy device meets the pre-programmed correlation with the weight sensed by the scale system, and, if it does not, determining whether the patient has exited the bed.

19. The method of claim 18, further comprising the step of:

in response to determining that the patient has not exited the bed, adjusting the pressure within the sleeve to match with the pre-programmed correlation to the weight of the patient.

20. The method of claim 18, further comprising the steps of:

in response to determining that the patient has exited the bed, provide an alert to a caregiver that the pneumatic therapy device is not being used properly and automatically charting the condition in an electronic medical records system.

21. The method of claim 18, further comprising the step of:

in response to determining that the patient has exited the bed, automatically charting the condition in an electronic medical records system.

22. The method of claim 16, further comprising the step of:

in response to determining that the patient has exited the bed, provide an alert to a caregiver that the pneumatic therapy device is not being used properly.

23. The method of claim 18, further comprising the step of:

alerting a caregiver when the pressure of the pneumatic therapy device exceeds a pre-programmed threshold for the particular patient.

\* \* \* \* \*